United States Patent
Byk et al.

(10) Patent No.: US 6,521,252 B1
(45) Date of Patent: Feb. 18, 2003

(54) TRANSFECTING COMPOUNDS WHICH ARE SENSITIVE TO REDUCING CONDITIONS, PHARMACEUTICAL COMPOSITIONS CONTAINING THEM AND THEIR APPLICATIONS

(75) Inventors: Gérardo Byk, Qyriat Ono (IL); Catherine Dubertret, Sevres (FR); Bruno Pitard, Brindas (FR); Daniel Scherman, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/610,727

(22) Filed: Jul. 6, 2000

Related U.S. Application Data

(63) Continuation of application No. PCT/FR99/00162, filed on Jan. 28, 1999.
(60) Provisional application No. 60/077,026, filed on Mar. 6, 1998.

(30) Foreign Application Priority Data

Jan. 30, 1998 (FR) .............................. 98 01065

(51) Int. Cl.[7] .............................. A61K 9/127
(52) U.S. Cl. .................. 424/450; 435/458; 514/44; 536/23.1
(58) Field of Search ................ 424/450; 435/458; 514/44; 536/23.1

(56) References Cited

U.S. PATENT DOCUMENTS

| | | | | |
|---|---|---|---|---|
| 5,942,634 A | * | 8/1999 | Siegel et al. | ........... 552/524 |
| 6,153,434 A | | 11/2000 | Hughes et al. | |

FOREIGN PATENT DOCUMENTS

| | | |
|---|---|---|
| EP | 394111 | 10/1990 |
| EP | 0747351 | 12/1998 |
| WO | 9305162 | 3/1993 |
| WO | 9610038 | 4/1996 |
| WO | 9617823 | 6/1996 |
| WO | 9625508 | 8/1996 |
| WO | 9718185 | 5/1997 |
| WO | 9929349 | 6/1999 |
| WO | 9114696 | 10/1999 |
| WO | 9958152 | 11/1999 |

OTHER PUBLICATIONS

Inder M. Verma et al, Gene therapy–promises,problems and prospects, Nature, vol. 389, Sep. 1997.*
W. French Anderson, Human gene therapy, Nature vol. 392, Apr. 30, 1998.*
Joseph Zabner et al., "Cellular and Molecular Barriers to Gene Gransfer by a Cationic Lipid", The Journal of Biological Chemistry, vol. 270, No. 32, Issue of Aug. 11, pp. 18997–19007, 1995.
Bruno Pitard, et al., "Virus–Sized Self–Assembling Lamellar Complexes Between Plasmid DNA and Cationic Micelles Promote Gene Gransfer", Proc. Natl. Acad. Sci. USA, vol. 94, pp. 14412–14417, Dec. 1997 Biophysics.
Gerardo Byk et al., One Pot Synthesis of Unsymmetrically Functionalized Polyamines by a Solid Phase Strategy Starting from their Symmetrical Polyamine–Counterparts, Tetrahedron Letters, vol. 38, No. 18, pp. 3219–3222, 1997.
Fuxing Tang et al., "Introduction of a Disulfide Bond into a Cationic Lipid Enhances Transgene Expression of Plasmid DNA", Biochemical and Biophysical Research Communications 242, 141–145, 1998, Article No. RC977923.
LA Cellule, Ed. Vigot et Decarie, 1988, pp. 581–583, (From "Des detergents sont utillises") (Partial translation).
Zabner, J. et al, Cellular and Molecular Barriers to Gene Transfer by a Cationic Lipid; J. Biol. Chem.; 1995 vol. 270; pp. 18997–19007.
LaCellule; Ed. Vigot and Décarie; 1988; pp. 581–583.
Pitard, B. et al; Proc. Natl. Acad. Sci USA; vol. 94; 1997; pp. 14412–14417.
Byk, G.; Frederic M.; and Scherman D.; Tetrahedron Letters; 1997; 38; pp. 3219–3222.
Tang, F. et al; "Use of Dithiodiglycolic Acid as a Tether for Cationic Lipids Decreases the Cytotoxicity and Increases Transgene Expression of Plasmid DNA in Vitro"; Biconjugate Chem.; vol. 10(5); 1999; pp. 791–791.
Tang, et al; "Cationic Liposomes Containing Disulfide Bonds in Delivery of Plasmid DNA"; J. of Liposome Res.; vol. 9(3); 1999; pp. 331–347.
Blessing, et al; "Monomolecular Collapse of Plasmid DNA into Stable Virus–like Particles"; PNAS; vol. 95; 1998; pp. 1427–1431.
Wadhwa, et al; "Peptide–Mediated Gene Delivery; Influence of Peptide Structure on Gene Expression"; Bioconjugate Chem.; vol 8(1), 1997; pp. 81–88.
Wilson, et al; The Journal of Biological Chemistry; vol. 267(2); 1992; pp. 963–967.
Alino, et al; Biochemical and Biophysical Research Communications; vol. 204(3); 1994; pp. 1023–1030.
Canonico, et al; American Journal of Respiratory Cell and Molecular Biol.; vol. 10; 1994; pp. 24–29.
Nabel, et al; Science, vol. 249; 1990; pp. 1285–1288.
Brigham, et al; American Journal of Respiratory Cell and Molecular Biol.; vol. 8; 1993; pp. 209–213.
Zhu, et al; Science; vol. 261; 1993; pp. 209–211.

(List continued on next page.)

*Primary Examiner*—James Ketter
(74) *Attorney, Agent, or Firm*—Irving Newman

(57) ABSTRACT

The invention concerns a novel agent for transferring nucleic acids into cells. Said agent is particularly characterised in that it comprises one or several disulphide bonds sensitive to reducing conditions. The invention also concerns compositions comprising such an agent for transferring in vivo, ex vivo or in vitro nucleic acids of interest into different cell types.

30 Claims, 9 Drawing Sheets

OTHER PUBLICATIONS

Figure 1:
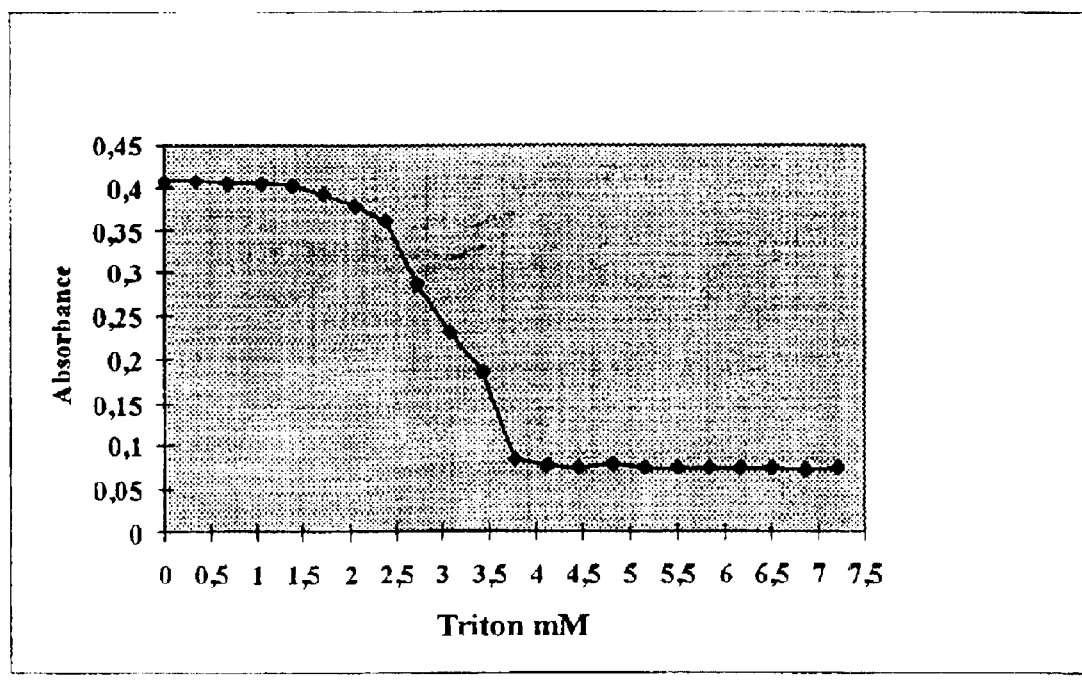

Gene Therapy for Cystic Fibrosis Using Cationic Liposome Mediated Gene Transfer: A Phase I Trial of Safety and Efficacy in the Nasal Airway; Human Gene Therapy; vol. 5, 1994; pp. 1259–1277.

Alam, et al; Reporter Genes; Application to the Study of mammalian Gene Transcription; Anal. Biochem; vol. 188; 1990; pp. 245–254.

Verma, et al; "Gene Therapy–promises, problems and prospects", Nature; vol. 389; Sep. 1997; pp. 239–242.

Anderson, W. French; "Human Gene Therapy"; Nature; vol. 392; Suppl; Apr. 1998; pp. 25–30.

Tang, et al; "Introduction of a Disulfide Bond into a Cationic Lipid Enhances Transgene Expression of Plasmid DNA"; Biochemical and Biophysical Research Communications; vol. 242(1); Jan. 1998; pp. 141–145.

* cited by examiner

FIGURE 3

|  | nmol/µg of DNA | RLU/5µl cellular extract/10s | RLU/µg protein/10s |
|---|---|---|---|
| Reference cationic lipid REF | 2 | 2.5 E+03 | 1.7 E+03 |
|  | 4 | 3.7 E+03 | 2.9 E+03 |
|  | 6 | 2.6 E+04 | 1.8 E+04 |
|  | 8 | 3.1 E+04 | 2.2 E+04 |
| Agent (VI) | 2 | 1.1 E+03 | 7.7 E+02 |
|  | 4 | 7.4 E+04 | 5.9 E+04 |
|  | 6 | 1.1 E+05 | 9.6 E+04 |
|  | 8 | 5.9 E+04 | 5.3 E+04 |

Tests on HepG2 cells

FIGURE 4

|  | nmol/µg of DNA | WITHOUT SERUM | | WITH SERUM | |
|---|---|---|---|---|---|
|  |  | RLU/5µl cellular extract/10s | RLU/µg protein/10s | RLU/5µl cellular extract/10s | RLU/µg protein/10s |
| Reference cationic lipid REF | 2 | 2.5 E+03 | 1.7 E+03 | 3.1 E+03 | 2.6 E+03 |
|  | 4 | 3.7 E+03 | 2.9 E+03 | 5.3 E+01 | 4.1 E+01 |
|  | 6 | 2.6 E+04 | 1.8 E+04 | 5.2 E+02 | 4.7 E+02 |
|  | 8 | 3.1 E+04 | 2.2 E+04 | 5.3 E+02 | 4.0 E+02 |
| Agent (I) | 2 | 3.4 E+03 | 2.4 E+03 | 1.4 E+03 | 1.2 E+03 |
|  | 4 | 4.7 E+03 | 3.7 E+03 | 2.6 E+03 | 2.3 E+03 |
|  | 6 | 1.1 E+04 | 8.7 E+03 | 8.3 E+03 | 7.2 E+03 |
|  | 8 | 4.4 E+04 | 3.3 E+04 | 1.5 E+04 | 1.2 E+04 |
| Agent (IV) | 2 | 5.9 E+03 | 4.4 E+03 | 2.5 E+03 | 2.2 E+03 |
|  | 4 | 1.3 E+05 | 1.0 E+05 | 3.0 E+04 | 2.6 E+04 |
|  | 6 | 2.2 E+05 | 1.7 E+05 | 4.4 E+04 | 4.1 E+04 |
|  | 8 | 2.2 E+05 | 1.8 E+05 | 6.7 E+04 | 5.7 E+04 |

Tests on HepG2 cells

|  | nmol/µg of DNA | WITHOUT SERUM | | WITH SERUM | |
|---|---|---|---|---|---|
|  |  | RLU/5µl cellular extract/10s | RLU/µg protein/10s | RLU/5µl cellular extract/10s | RLU/µg protein/10s |
| Reference cationic lipid REF | 2 | 2.9 E+05 | 1.6 E+05 | 1.5 E+05 | 7.8 E+04 |
|  | 4 | 2.2 E+06 | 1.7 E+06 | 6.8 E+03 | 3.5 E+03 |
|  | 6 | 3.4 E+06 | 2.8 E+06 | 1.7 E+04 | 9.2 E+03 |
|  | 8 | 4.3 E+06 | 3.5 E+06 | 2.8 E+04 | 1.5 E+04 |
| Agent (I) | 2 | 7.0 E+05 | 4.2 E+05 | 1.7 E+06 | 9.8 E+05 |
|  | 4 | 5.2 E+06 | 3.3 E+06 | 7.9 E+06 | 4.7 E+06 |
|  | 6 | 3.7 E+06 | 2.6 E+06 | 5.2 E+06 | 3.2 E+06 |
|  | 8 | 3.3 E+06 | 2.3 E+06 | 4.5 E+06 | 2.7 E+06 |
| Agent (IV) | 2 | 5.2 E+05 | 3.4 E+05 | 4.3 E+05 | 2.8 E+05 |
|  | 4 | 3.7 E+06 | 2.2 E+06 | 3.7 E+06 | 2.4 E+06 |
|  | 6 | 7.1 E+06 | 4.7 E+06 | 5.1 E+06 | 4.1 E+06 |
|  | 8 | 8.2 E+06 | 5.6 E+06 | 6.8 E+06 | 5.7 E+06 |

Tests on HeLa cells

FIGURE 7

|  | nmol/μg of DNA | WITHOUT SERUM | | WITH SERUM | |
|---|---|---|---|---|---|
|  |  | RLU/5μl cellular extract/10s | RLU/μg protein/10s | RLU/5μl cellular extract/10s | RLU/μg protein/10s |
| Reference cationic lipid REF | 2 | 2.5 E+03 | 1.7 E+03 | 3.1 E+03 | 2.6 E+03 |
|  | 4 | 3.7 E+03 | 2.9 E+03 | 5.3 E+01 | 4.1 E+01 |
|  | 6 | 2.6 E+04 | 1.8 E+04 | 5.2 E+02 | 4.7 E+02 |
|  | 8 | 3.1 E+04 | 2.2 E+04 | 5.3 E+02 | 4.0 E+02 |
| Agent (V) | 2 | 4.3 E+01 | 3.4 E+01 | 1.5 E+01 | 1.8 E+01 |
|  | 4 | 1.7 E+03 | 1.3 E+03 | 1.1 E+02 | 1.3 E+02 |
|  | 6 | 1.7 E+04 | 1.6 E+04 | 2.2 E+03 | 3.0 E+03 |
|  | 8 | 9.1 E+04 | 7.6 E+04 | 1.6 E+04 | 1.6 E+04 |

Tests on HepG2 cells

FIGURE 9

|  | nmol/μg of DNA | WITHOUT SERUM | | WITH SERUM | |
|---|---|---|---|---|---|
|  |  | RLU/5μl cellular extract/10s | RLU/μg protein/10s | RLU/5μl cellular extract/10s | RLU/μg protein/10s |
| Reference cationic lipid REF | 2 | 5.1 E+05 | 1.0 E+06 | 1.2 E+05 | 2.2 E+05 |
|  | 4 | 1.2 E+05 | 2.3 E+05 | 1.0 E+04 | 1.9 E+04 |
|  | 6 | 5.8 E+04 | 1.3 E+05 | 5.8 E+03 | 1.4 E+04 |
|  | 8 | 2.1 E+04 | 3.6 E+04 | 3.3 E+03 | 7.3 E+03 |
| Agent (V) | 2 | 2.0 E+04 | 3.9 E+04 | 2.6 E+04 | 4.6 E+04 |
|  | 4 | 1.3 E+05 | 2.3 E+05 | 5.4 E+04 | 9.0 E+04 |
|  | 6 | 1.8 E+05 | 3.3 E+05 | 6.1 E+04 | 1.1 E+05 |
|  | 8 | 3.2 E+05 | 6.0 E+05 | 7.1 E+04 | 1.3 E+05 |

Tests on HepG2 cells

|  | nmol/μg of DNA | WITHOUT SERUM | | WITH SERUM | |
|---|---|---|---|---|---|
|  |  | RLU/5μl cellular extract/10s | RLU/μg protein/10s | RLU/5μl cellular extract/10s | RLU/μg protein/10s |
| Reference cationic lipid REF | 2 | 2.2 E+06 | 1.2 E+06 | 3.0 E+06 | 1.5 E+06 |
|  | 4 | 5.9 E+06 | 3.4 E+06 | 5.1 E+03 | 2.0 E+03 |
|  | 6 | 4.0 E+06 | 2.6 E+06 | 9.5 E+03 | 3.8 E+03 |
|  | 8 | 1.2 E+06 | 6.8 E+05 | 4.2 E+03 | 1.6 E+03 |
| Agent (V) | 2 | 1.9 E+05 | 8.2 E+04 | 2.9 E+05 | 1.2 E+05 |
|  | 4 | 7.9 E+05 | 3.3 E+05 | 1.0 E+06 | 4.1 E+05 |
|  | 6 | 1.4 E+06 | 6.4 E+05 | 2.0 E+06 | 8.4 E+05 |
|  | 8 | 3.0 E+06 | 1.5 E+06 | 5.0 E+06 | 2.1 E+06 |

Tests on HeLa cells

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial sequence
<220> FEATURE:
<223> OTHER INFORMATION: Synthetic Construct

<400> SEQUENCE: 1

Lys Thr Pro Lys Lys Ala Cys Lys Pro
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic Construct

<400> SEQUENCE: 2

Ala Thr Pro Ala Lys Lys Ala Ala
1               5
```

TRANSFECTING COMPOUNDS WHICH ARE SENSITIVE TO REDUCING CONDITIONS, PHARMACEUTICAL COMPOSITIONS CONTAINING THEM AND THEIR APPLICATIONS

This is a continuation of International Patent Application No. PCT/FR99/00162, filed Jan. 28, 1999, which, in turn, claims priority from U.S. Provisional Patent Application No. 60/077,026, filed Mar. 6, 1998, and French Patent Application No. 98/01,065, filed Jan. 30, 1998.

The present invention relates to a new agent for transferring nucleic acids into cells. This transfer agent is more particularly characterized in that it contains one or more disulphide bridges which are sensitive to reducing conditions. This new agent can be used to transfer nucleic acids of interest into different cell types either in vitro, in vivo or ex vivo.

With the development of biotechnology, the possibility of effectively transferring nucleic acids into cells has become a necessity. It involves the transfer of nucleic acids into cells in vitro, for example, for the production of recombinant proteins, or in the laboratory for studying the regulation of the expression of genes, the cloning of genes, or any other manipulation involving DNA. It may also involve the transfer of nucleic acids into cells in vivo, for example for the creation of transgenic animals, the production of vaccines, labelling studies or also therapeutic approaches. It may also be the transfer of nucleic acids into cells ex vivo, in approaches including bone marrow transplants, immunotherapy or other methods involving the transfer of genes into cells collected from an organism for the purpose of their subsequent readministration.

The various synthetic vectors developed so far in order to improve the transfer of nucleic acids into cells possess a considerable structural diversity which reflects the observation of the fact that their efficiency is different depending on the desired application and the intended cell types. This efficiency is largely dependent on their structure.

Among the synthetic vectors developed hitherto, cationic lipids have an important place. These vectors consist of a cationic polar part which interacts with the nucleic acids, and a hydrophobic lipid part which enables the complex formed to be protected from the external medium. The following may be mentioned by way of example: the monocationic lipids (DOTMA: Lipofectin®); lipopolyamines, in particular dioctadecylamidoglycyl spermine (DOGS) or 5-carboxy-spermylamide of palmitoylphosphatidylethanolamine (DPPES), whose preparation has been described, for example, in Patent Application EP 394 111; or else the cationic lipids cited in Applications WO 96/17823 and WO 97/18185 (incorporated into the present by way of reference).

Many studies have clearly indicated that cationic lipids possess properties which make it possible to promote transfection. However, it now appears necessary to develop cationic lipids having novel structures which make it possible to provide additional beneficial properties. Thus, there is a need for cationic lipids which would be more particularly suitable for crossing membrane barriers. Indeed, numerous obstacles prevent a real transfection efficiency, among which the difficulty for the nucleic acid to cross biological membranes and to penetrate into the cellular compartments ("Cellular and Molecular Barriers to Gene Transfer by a Cationic Lipid", Zabner, J. et al., J. Biol. Chem., 1995, No. 32, 18997–19007). It is this technical difficulty which the present invention proposes to solve.

Thus, the present invention relates to novel nucleic acid transfer agents which comprise at least one cationic hydrophilic region capable of noncovalently combining with nucleic acids and at least one lipophilic region, these regions being connected to each other through a so-called "spacer" arm, and comprising, in addition, at least one disulphide bridge positioned such that its reduction causes partial degradation of the lipophilic region, or alternatively positioned such that its reduction causes separation of the said transfer agent when it is symmetrical.

These transfer agents are capable of efficiently complexing nucleic acids by virtue of their cationic hydrophilic parts, this interaction strongly compacting the said nucleic acid, and the lipophilic region makes this ionic interaction insensitive to the external medium by covering the particle formed with a lipid film.

However, in addition to these properties which are desired for vectorization, the transfer agents according to the invention possess an extremely advantageous detergent property, by generating, at the level of the reducing cellular medium, because of the presence of the disulphide bridge(s), molecules of the polyaminated alkyl chain type which are membrane destabilizers. Indeed, the disulphide bridges are capable of constituting stable covalent bonds in oxidizing medium, and of breaking in reducing medium, according to the following scheme:

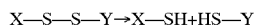

X—S—S—Y→X—SH+HS—Y

This type of structure is present, for example, in certain proteins possessing cysteine amino acids, and contributes to their three-dimensional structure and therefore to their biological activity. Disulphide bridges have, moreover, already been introduced into certain chimeric proteins, and in particular into immunotoxins, in order to connect the targeting domain to the active domain.

"Reducing medium" is understood to mean, for the purposes of the invention, a natural reducing medium, for example the intracellular medium, in particular the cytoplasm and in particular the endosomes. An artificial reducing medium representative of natural conditions is for example a medium comprising 0.1% to 20% of dithiotreitol (DTT).

By contrast, "oxidizing medium" is understood to mean any medium which is in contact with atmospheric oxygen and which contains no reducing agent, in particular the extracellular medium. A representative oxidizing medium for example consists of a 150 mM isotonic solution of sodium chloride, or of a solution containing 5% glucose.

The Applicant has thus demonstrated, quite unexpectedly, that one of the disulphide bridges could be introduced into a synthetic vector for the transfer of nucleic acids, in particular of the cationic lipid type, and that this did not affect its capacity to complex the nucleic acids in a non-reducing medium. It also shows that the nucleic acid transfer properties of these agents are preserved, or even improved. Moreover, the complexes formed are degraded in reducing medium, and therefore in particular in the cell, which makes it possible to generate detergent molecules, thus making a larger quantity of nucleic acid accessible to the cellular transcription machinery.

"Detergent" is understood to mean, for the purposes of the invention, any amphiphilic molecule having the property of being inserted into biological membranes and destabilizing them. This results from the capacity of detergents amphiphilic molecules to rupture the membranes by becoming inserted into the phospholipid double layers and by solubilizing the lipids and the proteins (La Cellule, Ed. Vigot and Décarie, 1988, pp. 581–583).

Another advantage of the transfer agents according to the invention also consists in their reduced intrinsic toxicity. Indeed, the transfer agent being degraded in the cell at the level of the disulphide bridges which are sensitive to reducing conditions, it does not exert the toxic effect observed for conventional transfer vectors. Furthermore, the improvement of the passage across the membranes allows the use of smaller doses of nucleic acid/transfer agent complex, with the beneficial consequences resulting therefrom on toxicity.

Finally, the Applicant has also demonstrated that the transfer properties are significantly improved when the lipophilicity of the transfer agents is sufficient and when they are used in adequate quantity. More particularly, it has been shown that one of the major advantages of increasing the lipophilicity of these agents, or of introducing a chain derived from a steroid, is the induction of improved resistance to serum.

The transfer agents according to the invention can have two types of structure, without this having an influence on their technical effect. In the first case, this structure can be represented in the following manner:

cationic hydrophilic region-spacer-lipophilic region

In such a structure, the disulphide bridge(s) are positioned in the lipophilic region so as to generate a detergent amphiphilic molecule when they are reduced.

The second type of structure can be represented as follows:

cationic hydrophilic region — spacer — lipophilic region
cationic hydrophilic region — spacer — lipophilic region In this case, the disulphide bridge(s) are positioned so that their reduction causes separation of the two symmetrical parts of the transfer agent, that is to say between the two spacer parts.

For the purposes of the invention, "cationic hydrophilic part" is understood to mean any hydrophilic molecule whose overall charge is positive at physiological pH, that is to say between pH 5 and 8, and possessing, in addition, properties of bonding with nucleic acids. This bond is in particular of the noncovalent bond type, such as for example ionic interactions. Preferably, the cationic hydrophilic region present in the transfer agents according to the invention is a polyamine or a polyaminoguanidine.

According to an advantageous variant, the cationic hydrophilic region corresponds to the following general formula:

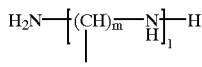

in which m is an integer greater than or equal to 2 and l is an integer greater than or equal to 1, it being possible for m to vary between the different groups of carbon between two amines. Preferably, m is between 2 and 6 inclusive, and l is between 1 and 5 inclusive. Still more preferably, the polyamine region is represented by spermine.

Another preferred polyamine region corresponds to the following general formula described in Application WO 97/18185:

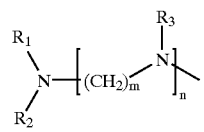

in which $R_1$, $R_2$ and $R_3$ represent, independently of each other, a hydrogen atom or a group —$(CH_2)_q$—$NRR'$ with q being capable of varying between 1, 2, 3, 4, 5 and 6 independently between the different groups $R_1$, $R_2$ and $R_3$, and R and R' represent, independently of each other, a hydrogen atom or a group —$(CH_2)_q$—$NH_2$ with q defined as above, and m and n represent, independently of each other, an integer capable of varying between 0 and 6 with, when n is greater than 1, m being capable of taking different values and $R_3$ different meanings in the above general formula.

The lipophilic region present in the transfer agents according to the invention consists of at least one fatty aliphatic chain and of one or more other aliphatic chains, of one or more steroid derivatives, of a natural or synthetic lipid, or optionally a combination of these, preferably capable of forming lamellar or hexagonal phases. These structures are characterized by the distances between the lamellae or the tubes which depend on the length of the fatty aliphatic chain or of the polar part of the lipid.

The term "fatty aliphatic chain" designates, for the purposes of the invention, a linear or branched alkyl chain comprising 10 to 22 carbon atoms, optionally saturated and/or fluorinated. Preferably, it comprises 12 to 22 carbon atoms. There may be mentioned more particularly the $C_{12}$, $C_{13}$, $C_{14}$, $C_{16}$, $C_{18}$ and $C_{19}$ aliphatic groups and the like, and in particular the $(CH_2)_{11}CH_3$, $(CH_2)_{12}CH_3$ $(CH_2)_{13}CH_3$, and $(CH_2)_{17}CH_3$ groups.

When the lipophilic region comprises a derivative of a steroid, the latter is preferably chosen from cholesterol, cholic acid or cholesterylamine.

In a preferred embodiment, the lipophilic region is composed of at least two fatty aliphatic chains. Still more preferably, it is composed of two or three fatty aliphatic chains.

According to another advantageous variant of the invention, the lipophilic part consists of a fatty aliphatic chain and a steroid derivative.

When the transfer agent according to the invention has a symmetrical structure, each symmetrical part of the molecule contains at least one fatty aliphatic chain.

The cationic hydrophilic region and the lipophilic region may be connected to each other through a so-called "spacer" arm. The spacer can be described, with no limitation being implied, as any acid or amine group comprising hydrolyzable functions, which is known to persons skilled in the art. Preferably, the so-called spacer region comprises an aliphatic or aromatic chain. Preferably, the spacer region may be, for example, chosen from amide, carbamate, ester or ether groups, or aromatic rings.

The transfer agents according to the invention comprise one or more disulphide bridges. The number of these bridges is determined by persons skilled in the art according to the structure of the transfer agent and the desired properties. Advantageously, the transfer agent comprises one or two disulphide bridges, and preferably one disulphide bridge. In the transfer agent, the disulphide bridge(s) may be positioned at different sites. The position depends on the number of bridges and the structure of the agent.

According to a first embodiment, the disulphide bridge is positioned such that its reduction causes partial degradation of the lipophilic region, thus generating a detergent amphiphilic molecule at the level of the cell. This partial degradation may correspond in particular to the loss of an aliphatic chain when the lipophilic region comprises several thereof, or alternatively the loss of the chain derived from a steroid when the lipophilic region contains one thereof. "Loss of an aliphatic fatty chain" is understood to mean either the complete loss thereof, or a partial loss, the remaining part, then being too short to constitute a fatty chain (length of less than 10 carbon atoms). Such a rupture destroys the integrity of the complex which then gradually disintegrates to give dissociated components of which at least one is a detergent amphiphilic molecule. The degradation of the complex can be easily checked by microscopy or by electrophoresis.

According to another variant, the disulphide bridge is positioned between the two spacer arms of a transfer agent of symmetrical structure, such that its reduction causes the separation of the said transfer agent.

According to another variant, the disulphide bridge is positioned between the two spacer arms of a transfer agent of symmetrical structure, such that its reduction causes the separation of the said transfer agent.

Preferred transfer agents according to the invention comprise:

as cationic hydrophilic region, a polyamine or polyaminoguanidine, as lipophilic region, at least two fatty aliphatic chains, or at least one chain derived from a steroid and one fatty aliphatic chain, and, a disulphide bridge whose reduction leads to the loss of a fatty aliphatic chain, or of a chain derived from a steroid when the transfer agent contains one.

In a particularly advantageous manner, the transfer agents of the invention comprise a polyamine region, three aliphatic chains of which at least two are fatty chains, and a disulphide bridge leading, in a reducing medium, to the loss of an aliphatic chain.

Other particularly advantageous transfer agents comprise a polyamine region, a fatty aliphatic chain and a chain derived from a steroid, and a disulphide bridge leading, in a reducing medium, to the loss of the chain derived from a steroid.

Other particularly advantageous transfer agents consist of two symmetric lipopolyamines, and of a disulphide bridge leading, in a reducing medium, to their separation.

Such agents are illustrated in the examples. The following compounds may be mentioned with no limitation being implied:

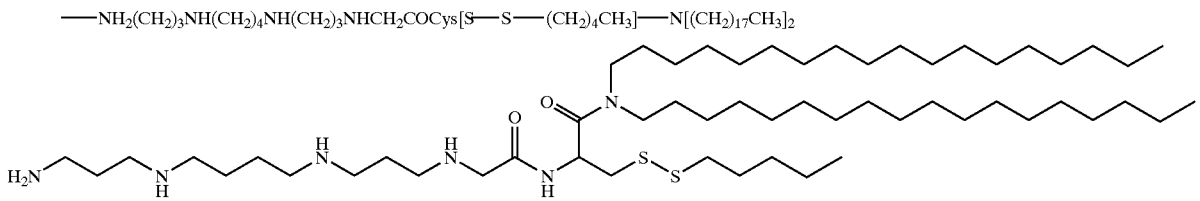

(I)

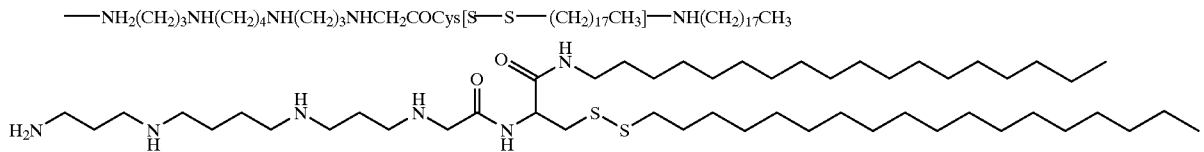

(II)

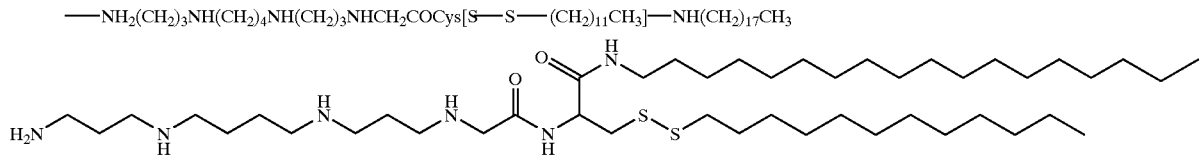

(III)

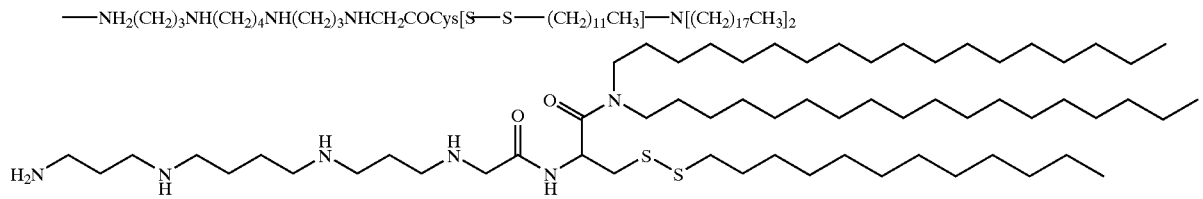

(IV)

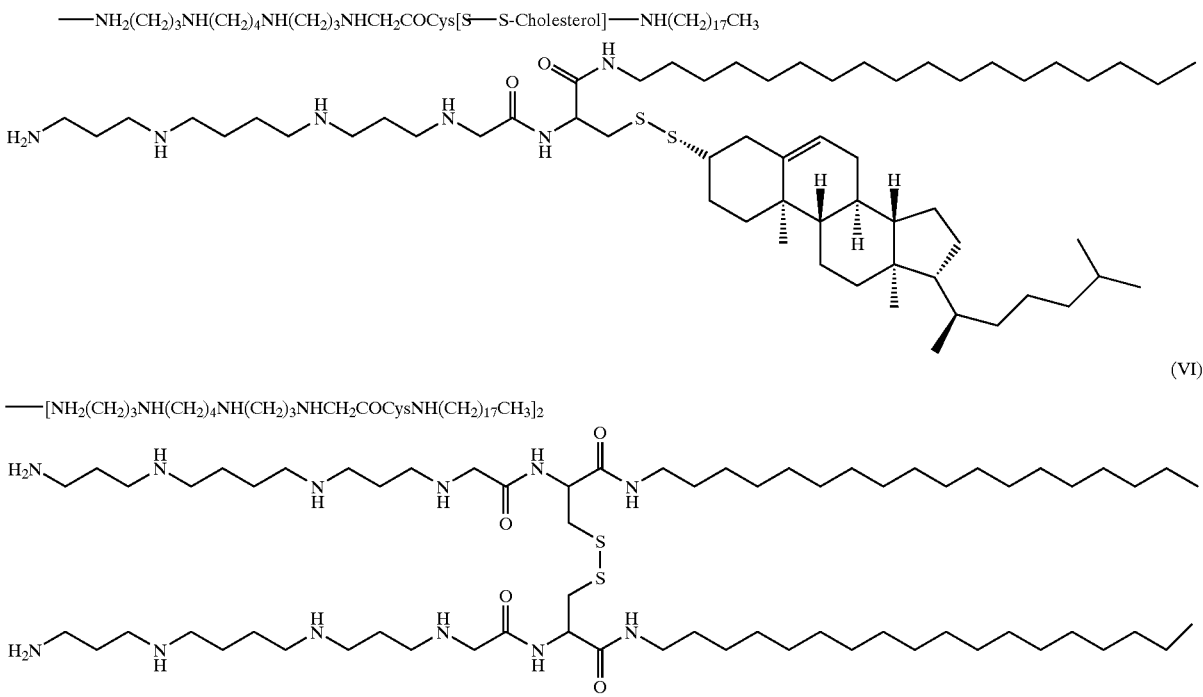

Another subject of the invention relates to a composition comprising a transfer agent as defined above, and at least one nucleic acid. Preferably, the transfer agent and the nucleic acid are present in quantities such that the ratio of the positive charges of the agent to the negative charges of the nucleic acid is between 0.1 and 50. This ratio can be easily adjusted by persons skilled in the art depending on the agent used, the nucleic. acid and the type of cells to be transfected. Advantageously, this ratio is between 3 and 12 nanomoles of agent according to the invention per μg of nucleic acid, and preferably between 3 and 9 nanomoles of transfecting agent per μg of nucleic acid.

For the purposes of the invention, "nucleic acid" is understood to mean both a deoxyribonucleic acid and a ribonucleic acid. They may be natural or artificial sequences, and in particular genomic DNA (gDNA), complementary DNA (cDNA), messenger RNA (mRNA), transfer RNA (tRNA), ribosomal RNA (rRNA), hybrid sequences or synthetic or semisynthetic sequences, oligonucleotides which are modified or otherwise. These nucleic acids may be of human, animal, plant, bacterial or viral origin and the like. They may be obtained by any technique known to persons skilled in the art, and in particular by the screening of libraries, by chemical synthesis or by mixed methods including the chemical or enzymatic modification of sequences obtained by the screening of libraries. They may be chemically modified, that is to say that they may be pseudonucleic acids (PNA), oligonucleotides modified by various chemical bonds (for example phosphorothioate or methyl phosphonate), or alternatively oligonucleotides which are functionalized, that is to say which are coupled with one or more molecules having distinct characteristic properties.

As regards more particularly deoxyribonucleic acids, they may be single- or double-stranded, as well as short oligonucleotides or longer sequences. In particular, the nucleic acids advantageously consist of plasmids, vectors, episomes, expression cassettes and the like. These deoxyribonucleic acids may carry genes of therapeutic interest, sequences for regulating transcription or replication, anti-sense sequences which are modified or otherwise, regions for binding to other cellular components, and the like.

Preferably, the nucleic acid comprises an expression cassette consisting of one or more genes of therapeutic interest under the control of one or more promoters and of a transcriptional terminator which are active in the target cells.

For the purposes of the invention, "gene of therapeutic interest" is understood to mean in particular any gene encoding a protein product having a therapeutic effect. The protein product thus encoded may be a protein, a peptide, and the like. This protein product may be homologous in relation to the target cell (that is to say a product which is normally expressed in the target cell when the latter has no pathological condition). In this case, the expression of a protein makes it possible, for example, to palliate an insufficient expression in the cell or the expression of a protein which is inactive or weakly active because of a modification, or to overexpress the said protein. The therapeutic gene may also encode a mutant of a cellular protein, having increased stability, a modified activity and the like. The protein product may also be heterologous in relation to the target cell. In this case, an expressed protein may, for example, supplement or provide an activity which is deficient in the cell, allowing it to combat a pathological condition, or to stimulate an immune response.

Among the products of therapeutic interest for the purposes of the present invention, there may be mentioned more particularly enzymes, blood derivatives, hormones, lymphokines [interleukins, interferons, TNF, and the like (FR 9,203,120)], growth factors, neurotransmitters or their precursors or synthesis enzymes, trophic factors [BDNF, CNTF, NGF, IGF, GMF, aFGF, bFGF, NT3, NT5, HARP/pleiotrophin, and the like], dystrophin or a minidystrophin (FR 91/11947), the CFTR protein associated with cystic fibrosis, tumour suppressor genes [p53, Rb, Rap1A, DCC, k-rev, and the like (FR 93/04745)], genes encoding factors involved in coagulation [factors VII, VIII, IX], the genes involved in DNA repair, suicide genes [thymidine kinase, cytosine deaminase], the genes for haemoglobin or other protein carriers, the genes corresponding to the proteins involved in the metabolism of lipids, of the apolipoprotein type chosen from apolipoproteins A-I, A-II, A-IV, B, C-I, C-II, C-III, D, E, F, G, H, J and apo(a), metabolic enzymes such as for example lipoprotein lipase, hepatic lipase, lecithin cholesterol acyl transferase, 7-alpha-cholesterol hydroxylase, phosphatidic acid phosphatase, or lipid transfer proteins such as the cholesterol ester transfer protein and the phospholipid transfer protein, an HDL-binding protein or a receptor chosen, for example, from the LDL receptors, the remnant chylomicron receptors and the scavenger receptors, and the like.

The therapeutic nucleic acid may also be a gene or an anti-sense sequence, whose expression in the target cell makes it possible to control the expression of genes or the transcription of cellular mRNAs. Such sequences can, for example, be transcribed in the target cell into RNAs which are complementary to cellular mRNAs and thus block their translation to protein, according to the technique described in Patent EP 140 308. The therapeutic genes also comprise the sequences encoding ribozymes, which are capable of selectively destroying target RNAs (EP 321 201).

As indicated above, the nucleic acid may also comprise one or more genes encoding an antigenic peptide, which is capable of generating an immune response in humans or in animals. In this specific embodiment, the invention therefore allows the production of vaccines or the carrying out of immunotherapeutic treatments applied to humans or to animals, in particular against microorganisms, viruses or cancers. They may be in particular antigenic peptides specific for the Epstein-Barr virus, the HIV virus, the hepatitis B virus (EP 185 573), the pseudo-rabies virus, the syncitia forming virus, other viruses, or specific for tumours (EP 259 212).

Preferably, the nucleic acid also comprises sequences allowing the expression of the therapeutic gene and/or the gene encoding the antigenic peptide in the desired cell or organ. They may be sequences which are naturally responsible for the expression of the gene considered when these sequences are capable of functioning in the infected cell. They may also be sequences of different origin (responsible for the expression of other proteins, or even synthetic). In particular, they may be promoter sequences of eukaryotic or viral genes. For example, they may be promoter sequences derived from the genome of the cell which it is desired to infect. Likewise, they may be promoter sequences derived from the genome of a virus. In this regard, there may be mentioned, for example, the promoters of the E1A, MLP, CMV and RSV genes, and the like. In addition, these expression sequences may be modified by the addition of activating or regulatory sequences, and the like. The promoter may also be inducible or repressible.

Moreover, the nucleic acid may also comprise, in particular upstream of the therapeutic gene, a signal sequence directing the therapeutic product synthesized in the secretory pathways of the target cell. This signal sequence may be the natural signal sequence of the therapeutic product, but it may also be any other functional signal sequence, or an artificial signal sequence. The nucleic acid may also comprise a signal sequence directing the synthesized therapeutic product towards a particular compartment of the cell.

The compositions may, in addition, comprise adjuvants capable of combining with the transfer agent/nucleic acid complex and of improving its transfecting power.

In this regard, the compositions according to the invention may comprise, as adjuvant, one or more neutral lipids. Such compositions are particularly advantageous, in particular when the ratio of the positive charges of the agent to the negative charges of the nucleic acid is low. The Applicant has indeed shown that the addition of a neutral lipid makes it possible to improve the formation of nucleolipid particles and, surprisingly, to promote cellular penetration by destabilizing the membrane.

More preferably, the neutral lipids used within the framework of the present invention are lipids containing two fatty chains.

In a particularly advantageous manner, natural or synthetic lipids which are zwitterionic or lacking ionic charge under physiological conditions are used. They may be chosen more particularly from dioleoyl-phosphatidylethanolamine (DOPE), oleoylpalmitoyl-phosphatidylethanolamine (POPE), di-stearoyl, -palmitoyl, -cholesteryl, -myristoylphosphatidylethanolamines as well as their derivatives which are N-methylated one to three times, phosphatidyl glycerols, glycosyldiacylglycerols, cerebrosides (such as in particular galactocerebrosides), sphingolipids (such as in particular sphingomyelins), or asialogangliosides (such as in particular asialoGM1 and GM2). These different lipids may be obtained either by synthesis or by extraction from organs (for example the brain) or from eggs, by conventional techniques well known to persons skilled in the art. In particular, the extraction of the natural lipids may be carried out by means of organic solvents (see also Lehninger Biochemistry).

More recently, the Applicant has demonstrated that it was also particularly advantageous to use, as adjuvant, a compound directly involved or otherwise in the condensation of the said nucleic acid, such as those cited in Application WO 96/25508. The presence of such a compound in a lipopolyamine-based transfecting composition makes it possible to considerably reduce the quantity of this agent, with the beneficial consequences resulting therefrom from the toxicological point of view, without any damaging effect on the transfecting activity of the said composition. "Compound involved in the condensation of the nucleic acid" is intended to define a compound which compacts, directly or otherwise, the nucleic acid. More precisely, this compound may either act directly at the level of the nucleic acid to be transfected, or may be involved at the level of an additional compound which is directly involved in the condensation of this nucleic acid. Preferably, it acts directly at the level of the nucleic acid. In particular, the precompacting agent may be any polycation, for example polylysine. According to a preferred embodiment, this agent which is involved in the condensation of the nucleic acid is derived, as a whole or in part, from a protamine, a histone, a nucleolin and/or one of their derivatives. Such an agent may also consist, as a whole or in part, of peptide units (KTPKKAKKP) and/or (ATPAKKAA), it being possible for the number of units to vary between 2 and 10. In the structure of the compound according to the invention, these units may be repeated continuously or otherwise. They may thus be separated by linkages of a biochemical nature, for example one or more amino acids, or of a chemical nature.

Preferably, the compositions of the invention comprise from 0.01 to 20 equivalents of adjuvant per equivalent of nucleic acids in weight/weight, and more preferably from 0.5 to 5.

The compositions according to the invention may also involve one or more targeting elements which make it possible to direct the nucleic complexes towards receptors or ligands at the surface of the cell. By way of example, the composition of the present invention may comprise one or more antibodies directed against cell surface molecules, or one or more membrane receptor ligands such as insulin, transferrin, folic acid or any other growth factor, cytokines or vitamins. Advantageously, the composition may use lectins, modified or otherwise, in order to target particular polysaccharides at the surface of the cell or on the neighbouring extracellular matrix. Proteins with an RGD unit, peptides containing a tandem of RGD units, which is cyclic or otherwise, as well as polylysine peptides, can be used. More recently, natural or synthetic ligand peptides have also been described which are advantageous in particular for their selectivity towards specific cells and which are capable of efficiently promoting internalization in these cells (Bary et al., Nature Medicine, 2, 1996, 299–305). These targeting agents are generally conjugated to the cationic transfection agent considered.

The invention also extends to any composition as defined above and comprising, in addition, one or more other agents known for transfecting the nucleic acid. In particular, there may be mentioned the products described in the Patent EP 394 111 and in Patent Applications WO 96/17823, or WO 97/18185 (incorporated into the present by way of reference).

Another subject of the present invention also relates to the use of a transfer agent as defined above for transferring nucleic acids into cells.

The compositions comprising the transfer agent according to the invention can be formulated for administration by the topical, cutaneous, oral, rectal, vaginal, parenteral, intranasal, intravenous, intramuscular, subcutaneous, intraocular, transdermal, intratracheal or intraperitoneal route, and the like. Preferably, the pharmaceutical compositions of the invention contain a vehicle which is pharmaceutically acceptable for an injectable formulation, in particular a direct injection into the desired organ, or for administration by the topical route (on the skin and/or the mucous membrane). They may be in particular isotonic sterile solutions, or dry, in particular freeze-dried, compositions which, upon addition, depending on the case, of sterilized water or of physiological saline, allow the constitution of injectable solutions. The nucleic acid doses used for the injection as well as the number of administrations may be adapted according to various parameters, and in particular according to the mode of administration used, the relevant pathological condition, the gene to be expressed, or the desired duration of treatment. As regards more particularly the mode of administration, it may be either a direct injection into the tissues or the circulatory system, or a treatment of cells in culture followed by their reimplantation by injection or transplantation.

The invention relates, in addition, to a method of transferring nucleic acids into cells comprising the following steps:

(1) bringing the nucleic acid into contact with a transfer agent as defined above., to form a nucleic acid/transfer agent complex, (2) bringing the cells into contact with the complex formed in (1).

In the case of a composition comprising one or more other transfection agents and/or one or more adjuvants, step (1) is preceded by a step of bringing the different transfection agents into contact and/or by a step of bringing the transfection agent into contact with the adjuvant(s)

The agent according to the invention/nucleic acid complexes are formed by mixing, volume for volume, two solutions, one containing the transfection agent according to the invention in the form of micelles or of a hexagonal lamellar phase, the other the nucleic acid to be transfected. The complexes are formed within a few seconds. They may be negatively or positively charged or they may be neutral, depending on the quantity of lipid added to the nucleic acid (Pitard B. et al., *Proc. Natl. Acad. Sci. USA*, Vol. 94, pp. 14412–14417, December 1997). The sizes of these complexes vary between 50 and 300 nm in diameter (measured by a quasielastic diffusion of light and by transmission electron microscopy). Moreover, the morphology of the complexes varies with the charge ratio R (ratio of the positive charges provided by the cationic lipid to the negative charges provided by the nucleic acid). For example, the negatively charged complexes are surrounded by molecules of nucleic acid. Moreover, the positively charged complexes have cationic lipids at their surface. As for the neutral complexes, they are. colloidally unstable. The Applicant has thus shown that it was possible to stabilize them by adding a non-ionic surfactant in a sufficient quantity. Preferred surfactants are in particular poloxamers, polyoxyethylene alcohols, polyoxyethylene nonyl phenyl ether or PEGs (polyethylene glycols) with a dendritic benzyl polyether head.

The cells are brought into contact with the complex by incubating the. cells. with the said complex (for uses in vitro or ex vivo), or by injecting the complex into an organism (for uses in vivo). The incubation is carried out preferably in the presence, for example, of 0.01 to 1000 $\mu$g of. nucleic acid per $10^6$ cells. For in vivo administration, doses of nucleic acids ranging from 0.01 to 10 mg may be used.

The transfer agents according to the invention are particularly advantageous for their use in transferring nucleic acids into primary cells or into established lines. These may be friboblast cells, muscle cells, nerve cells (neurons, astrocytes, glial cells), hepatic cells, haematopoietic cells (lymphocytes, CD34, dendritic cells, and the like), epithelial cells and the like in diffentiated or pluripotent form (precursors).

The present invention thus provides a particularly advantageous method for the treatment of diseases comprising the in vivo, ex vivo or in vitro administration of a nucleic acid capable of correcting the said disease, combined with a compound according to the invention. More particularly, this method is applicable to diseases resulting from a deficiency in or a lack of protein or nucleic product. The administered nucleic acid encodes the said protein product or contains the said nucleic product.

In addition to the preceding arrangements, the present invention also comprises other characteristics and advantages which will emerge from the examples and figures which follow, and which should be considered as illustrating the invention without limiting the scope thereof. In particular, the Applicant proposes, with no limitation being implied, various operating protocols as well as reaction intermediates which can be used to prepare the transfer agents according to the invention. of course, it is within the capability of persons skilled in the art to draw inspiration from these protocols or intermediate products in order to develop similar methods so as to lead to these same compounds.

FIGURES

FIG. 1: Curve representing the profile for solubilization of liposomes EPC/EPA (10:1) by Triton X-100 by measurement of the turbidity of the solution with the aid of a spectrophotometer. The quantity of Triton X-100 added in mM is represented on the x-axis. The absorbance of the solution containing the liposomes is measured on the y-axis.

Figure 2:
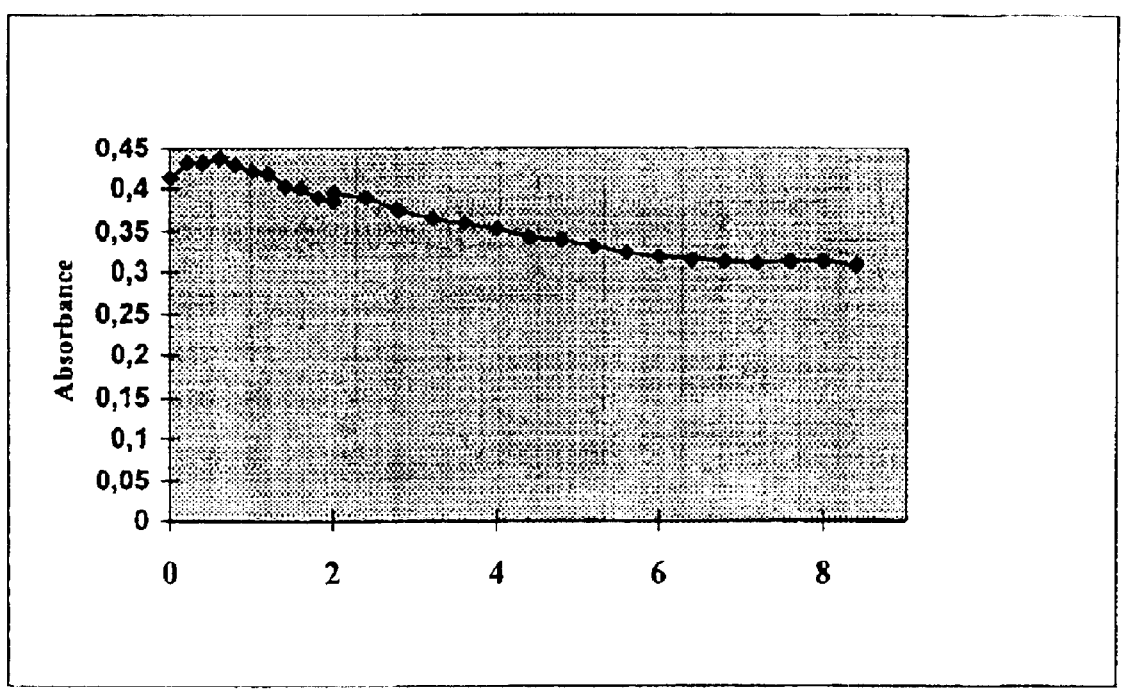

FIG. 2: Curve representing the profile for solubilization of liposomes EPC/EPA (10:1) by compound (VII) by measurement of the turbidity of the solution with the aid of a spectrophotometer. The quantity of compound (VII) added in mM is represented on the x-axis. The absorbance of the solution containing the liposomes is measured on the y-axis.

FIG. 3: Activity of transfection of the compound (VI) into HepG2 cells in the absence of serum, compared with the cationic lipid of formula $H_2N(CH_2)_3NH(CH_2)_4NH(CH_2)_3NHCH_2COGly[(CH_2)_{17}CH_3]_2$ used as reference transfer agent (called REF in the remainder of the application).

FIG. 4: Activity of transfection of the compound (I) and of the compound (IV) into HepG2 and HeLa cells, in the presence and in the absence of serum, compared with the reference cationic lipid REF.

Figure 5:
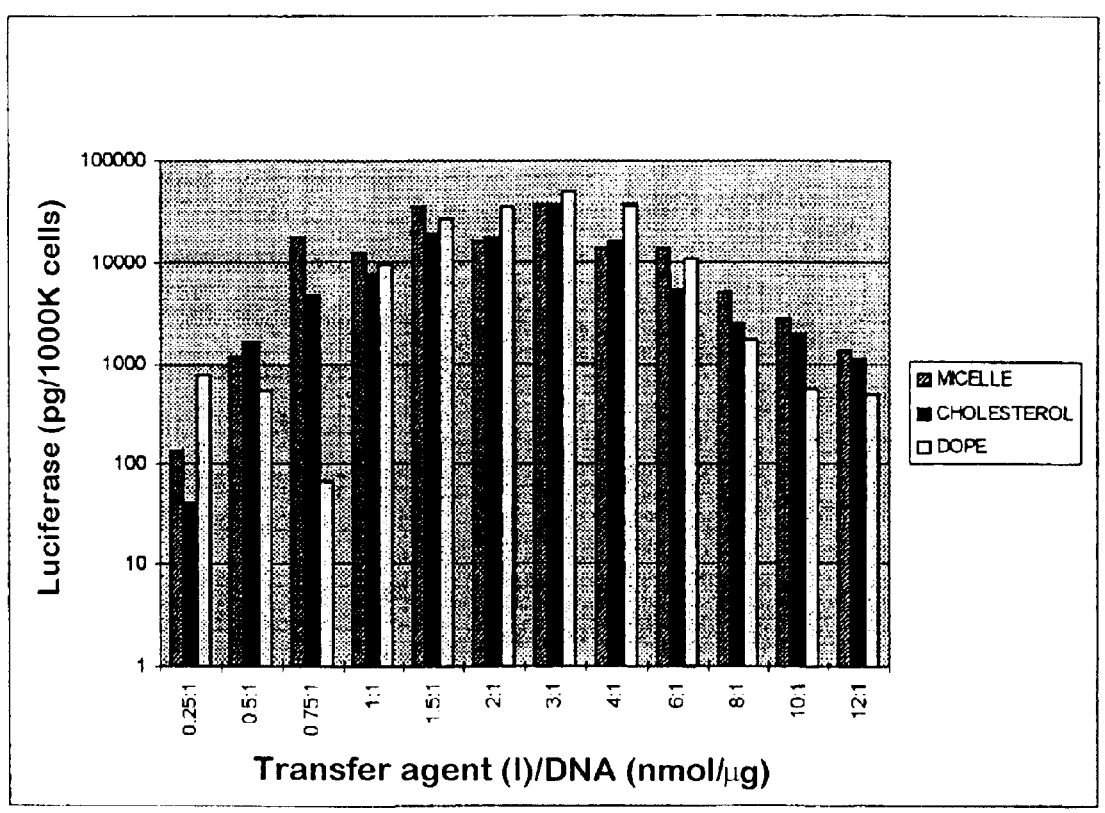

FIG. 5: Histogram representing the activity of in vitro transfer into HeLa cells of the compound (I) without co-lipid or alternatively in the presence of a co-lipid DOPE or cholesterol. The y-axis represents the expression of luciferase in pg per well. The x-axis indicates the compound (I)/DNA ratio in nmol/µg of DNA.

Figure 6:
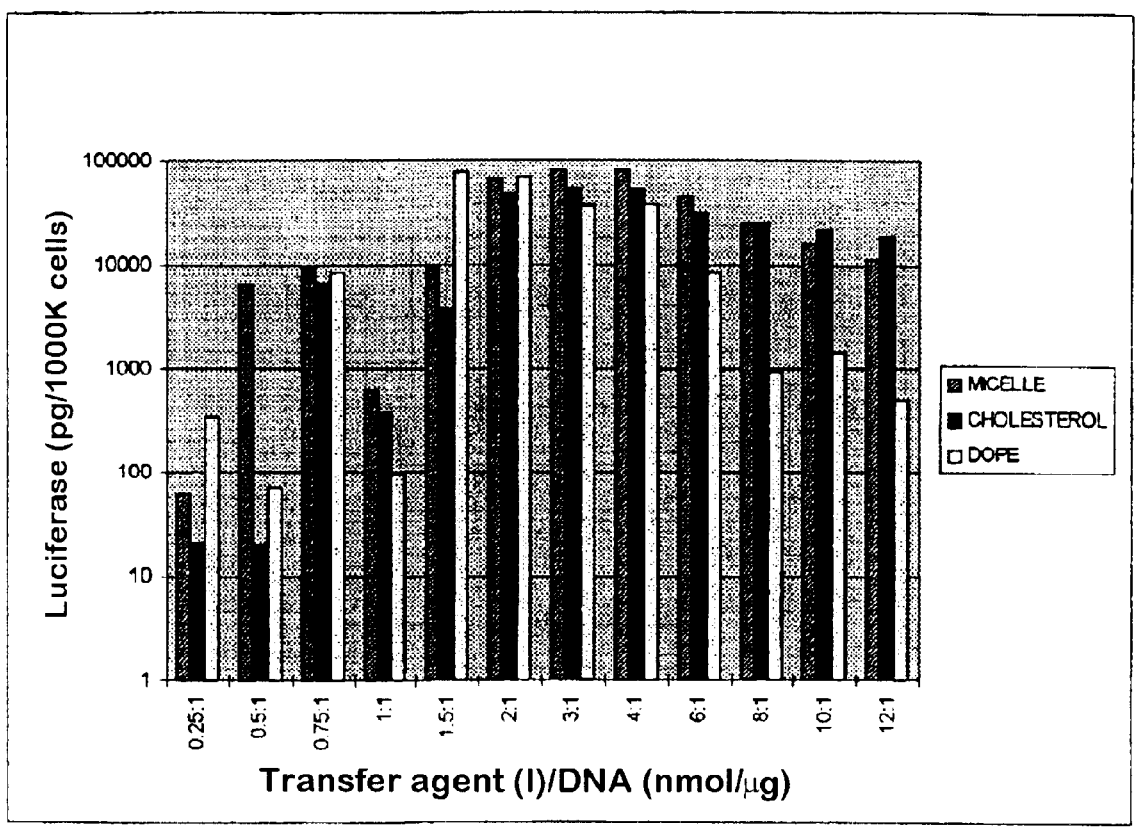

FIG. 6: Histogram representing the activity of in vitro transfer into HeLa cells of the compound (IV) without co-lipid or alternatively in the presence of a co-lipid DOPE or cholesterol. The y-axis represents the expression of luciferase in pg per well. The x-axis indicates the compound (IV)/DNA ratio in nmol/µg of DNA.

FIG. 7: Activity of transfection of the compound (II) into HepG2 cells, in the presence and in the absence of serum, compared with-the reference cationic lipid REF.

Figure 8:
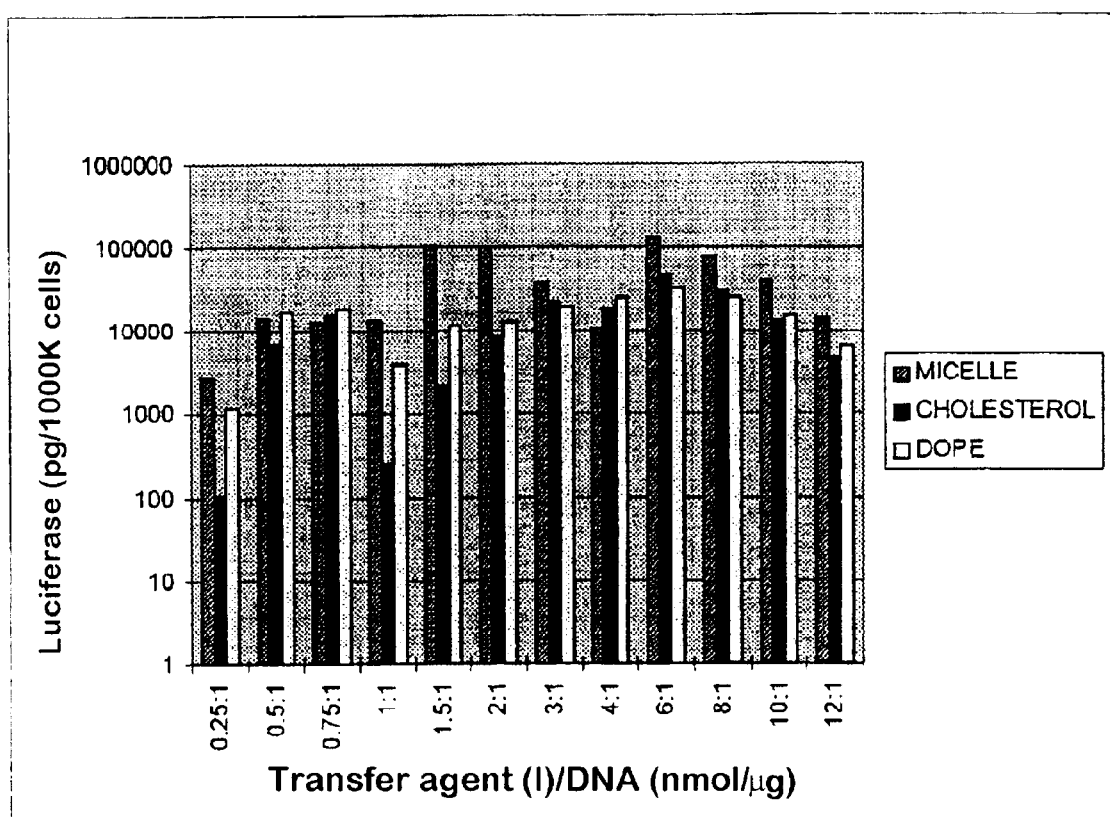

FIG. 8: Histogram representing the activity of in vitro transfer into HeLa cells of the compound (II) without co-lipid or alternatively in the presence of a co-lipid DOPE or cholesterol. The y-axis represents the expression of luciferase in pg per well. The x-axis indicates the compound (II)/DNA ratio in nmol/µg of DNA.

FIG. 9: Activity of transfection of the compound (V) into HepG2 and HeLa cells, in the presence and in the absence of serum, compared with the reference cationic lipid REF.

EXAMPLES

Example 1

Chemical Syntheses of the Transfer Agents
According to the Invention

A. MATERIALS

Triethylamine, N-ethyldiisopropylamine, dioctadecylamine, $N_\alpha,N_{\alpha'}$-diBoccystine, and the BOP reagent are available commercially. Likewise for amylamine, octadecylamine, penthanethiol, dodecanethiol, octadecanethiol and thiocholesterol.

$BocNH(CH_2)_3$ $NBoc(CH_2)_4$ $NBoc(CH_2)_3$ $NBocCH_2CO_2H$ was synthesized in the laboratory according to the procedure described in Application WO 97/18185 and in the article Byk G., Frederic M., and Scherman D., Tetrahedron Letters (1997) 38, 3219–3222.

B. METHODS a) Spectroscopic Analyses

The proton NMR spectra (Nuclear Magnetic Resonance) were recorded on Brucker 250 and 400 MHz spectrometers.

b) Chromatography Techniques

The HPLC (High Performance Liquid Chromatography) Analyses are carried out on a HITACHI apparatus equipped with an autosampler AS-2000A, a pump L-6200A, a UV detector L 4000 at 220 nm, and an integrator-calculator D 2500. The column used, marketed by APPLIED BIOSYSTEMS, is made of stainless steel 3 cm long and 4.6 mm in diameter. The mobile phases are water and acetonitrile supplemented with trifluoroacetic acid, and the stationary phase is Aquapore butyl 7 micron. The flow rate varies between 1 and 4 ml/min.

The thin-layer chromatographies (TLC) are performed on 20×20 aluminium plates coated with silica gel.

c) Preparative HPLC Purification

The equipment used is a set for liquid-phase chromatography in gradient mode, allowing UV detection. This preparative chain is composed of:

Pump A: GILSON model 305, equipped with a 50 SC head.

Pump B: GILSON model 303, equipped with a 50 SC head.

Injection pump.: GILSON model 303, equipped with a 25 SC head.

Pressure module: GILSON model 806.

Mixer: GILSON model 811 C equipped with a 23 ml head.

UV Detector: GILSON model 119, equipped with a preparative cell, and set at 220 nm.

Fraction collector: GILSON model 202, equipped with No. 21 racks.

Integrator: SHIMADZU model C-R6A.

Column: Column C4 (10 mm) made of stainless steel 25 cm long and 2.2 cm in diameter, marketed by VYDAC model 214 TP 1022.

The solution of product to be purified is loaded onto the column by the injection pump at the flow rate of 15 ml/min. The mobile phases are water and acetonitrile.

C. CHEMICAL SYNTHESES a) Lipopolyamines with Fatty Chains Which can be Reduced by Their Disulphide Bridge These molecules have the general structure:

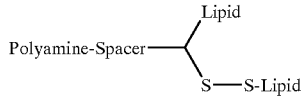

They were constructed in the following manner:

Step 1)

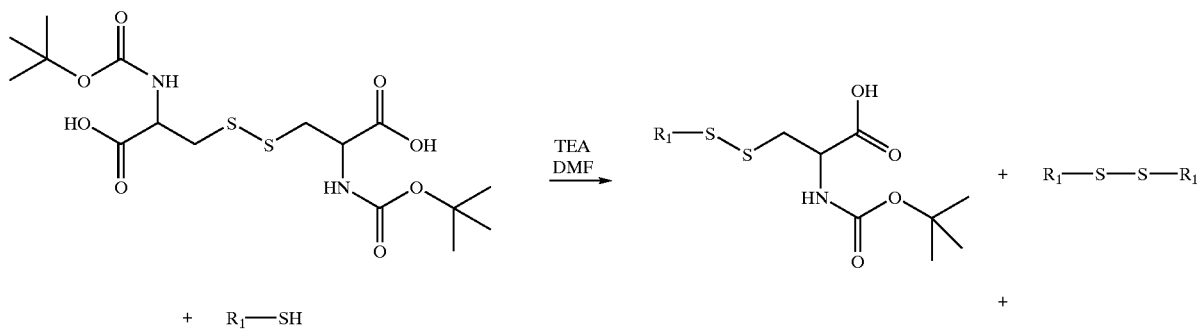

Step 2)

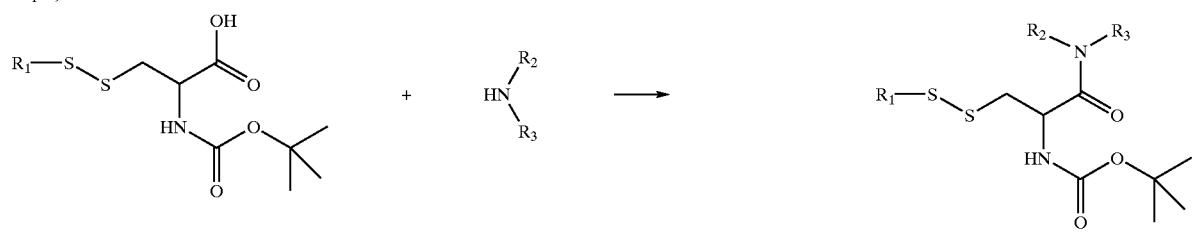

Step 3)

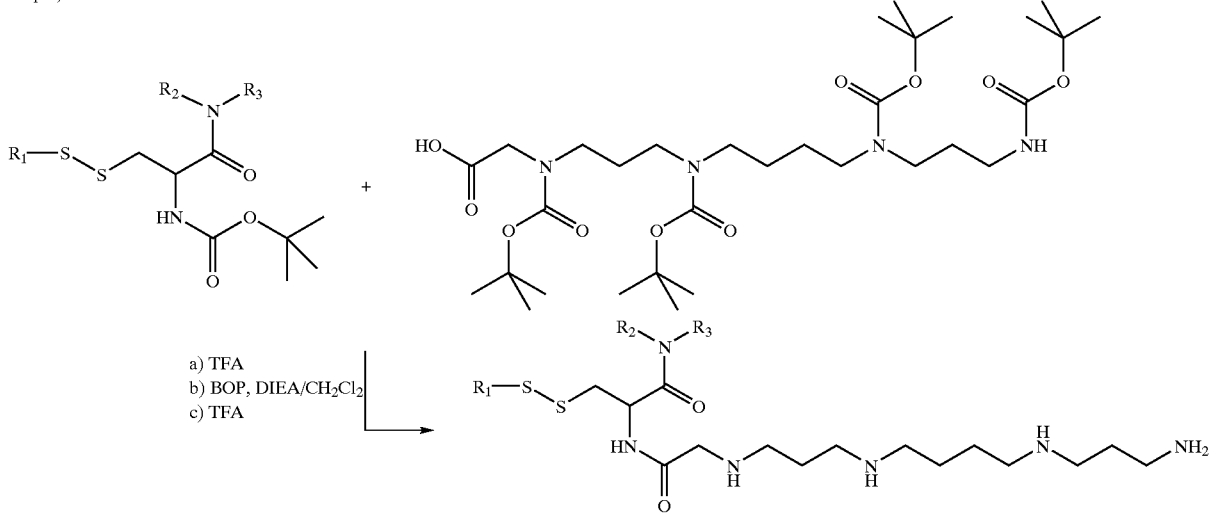

a) TFA
b) BOP, DIEA/CH₂Cl₂
c) TFA

The following non-limiting examples illustrate these transfer agents:

compound (I): $R_1=(CH_2)_4CH_3$; $R_2=(CH_2)_{17}CH_3$; $R_3=(CH_2)_{17}CH_3$ [preparation 3.1]

compound (II): $R_1=(CH_2)_{17}CH_3$; $R_2=(CH_2)_{17}CH_3$; $R_3=H$ [preparation 3.2]

compound (III): $R_1=(CH_2)_{11}CH_3$; $R_2=(CH_2)_{17}CH_3$; $R_3=H$ [preparation 3.3]

compound (IV): $R_1=(CH_2)_{11}CH_3$; $R_2=(CH_2)_{17}CH_3$; $R_3=(CH_2)_{17}CH_3$ [preparation 3.4]

compound (V): $R_1$=cholesteryl; $R_2=(CH_2)_{17}CH_3$; $R_3=H$ [preparation 3.5]

STEP 1

PREPARATION 1.1: NHBocCys[S—S—(CH₂)₄CH₃]—OH $N_\alpha,N_\alpha'$-diBoc-cystine (6.81 mmol) is dissolved in dimethylformamide (20 cm³). Triethylamine (58.1 mmol) is added to this solution followed by 1-pentanethiol (6.81 mmol). The mixture is stirred for 2 hours at room temperature. The triethylamine is evaporated and the concentrate is then added to a 0.5 M potassium sulphate (KHSO$_4$) solution (300 cm$^3$). The product which precipitates is extracted with 3 times 100 cm$^3$ of chloroform. The organic phases are combined and dried over anhydrous magnesium sulphate, and then the chloroform is evaporated off. The dry extract is solubilized with diethyl ether (100 cm$^3$) and is then extracted with 3 times 50 cm$^3$ of a saturated sodium carbonate (NaHCO$_3$) solution. The pooled aqueous phases are neutralized by adding, up to pH=3, a 0.5 M KHSO$_4$ solution (350 cm$^3$). The product which precipitates is extracted with 3 times 100 cm$^3$ of chloroform. The pooled organic phases are washed with twice 50 cm$^3$ of a saturated sodium chloride (NaCl) solution and then dried over anhydrous magnesium sulphate. The chloroform is evaporated off in a rotary evaporator. The product obtained is eluted with a chloroform/methanol mixture (9/1 v/v) on a silica column.

2.31 mmol of product are obtained, that is a yield of 34%. TLC Rf=0.63 (CHCl$_3$/MeOH, 9:1)

PREPARATION 1.2: NHBocCys[S—S—(CH$_2$)$_{17}$CH$_3$]—OH

N$_\alpha$,N$_\alpha$'-diBoc-cystine (6.81 mmol) is dissolved in dimethylformamide (20 cm$^3$). Triethylamine (58.1 mmol) is added to this solution followed by 1-octadecanethiol (6.81 mmol). The mixture is stirred for 2 hours at 40° C. The triethylamine is evaporated off in a rotary evaporator and the concentrate is then added to a 0.5 M KHSO$_4$ solution (300 cm$^3$). The product which precipitates is extracted with 3 times 100 cm$^3$ of chloroform. The organic phases are combined and dried over anhydrous magnesium sulphate and then the chloroform is evaporated off. The dry extract is solubilized with diethyl ether (100 cm$^3$) and is then washed with 3 times 50 cm$^3$ of a saturated NaHCO$_3$ solution. The ethereal phase is acidified by beating with twice 100 cm$^3$ of a 0.5 M KHSO$_4$ solution and then washed with twice 50 cm$^3$ of a saturated NaCl solution. The ethereal phase is dried over anhydrous magnesium sulphate and is then evaporated to dryness in a rotary evaporator. The crude product obtained is crystallized from petroleum ether.

1.36 mmol of product are obtained (Y=20%). TLC Rf=0.67 (CHCl$_3$/MeOH, 9:1), HPLC Rt=17.80 min.

PREPARATION 1.3: NHBocCys[S—S-Cholesterol]—OH

The synthesis is identical to preparation 1.2 but using thiocholesterol.

A yield of 58% is obtained. TLC Rf=0.59 (CHCl$_3$/MeOH, 9:1), HPLC Rt=19.16 min.

PREPARATION 1.4: NHBocCys[S—S—(CH$_2$)$_{11}$CH$_3$]—OH

The synthesis is identical to preparation 1.2 but at room temperature and using 1-dodecanethiol. A yield of 40% is obtained. TLC Rf=0.69 (CHCl$_3$/MeOH, 9:1), HPLC Rt=13.23 min.

STEP 2

PREPARATION 2.1: NHBocCys [S—S—(CH$_2$)$_4$CH$_3$]—N[(CH$_2$)$_{17}$CH$_3$]$_2$

The product obtained in 1.1 (1.15 mmol) is dissolved in dichloromethane (10 cm$^3$) and N-ethyldiisopropylamine (2.86 mmol), dioctadecylamine (1.15 mmol) and BOP (1.27 mmol) are added.

The mixture is stirred for 2 hours and monitored by TLC and HPLC.

The dichloromethane is evaporated off in a rotary evaporator. The "crude product" is taken up in chloroform (100 ml) and then washed successively with 3 times 50 cm$^3$ of 0.5 M KHSO$_4$, and then with 3 times 50 cm$^3$ of a saturated NaHCO$_3$ solution, and finally with twice 50 cm$^3$ of a saturated NaCl solution. The organic phase is dried over anhydrous magnesium sulphate and then the chloroform is evaporated off in a rotary evaporator. A yield of 64% is obtained.

TLC Rf=0.90 (CHCl$_3$/MeOH, 9:1), HPLC Rt=25.96 min.

PREPARATION 2.2: NHBocCys[S—S—(CH$_2$)$_{17}$CH$_3$]—NH(CH$_2$)$_{17}$CH$_3$

The synthesis is identical to preparation 2.1 but using the product obtained in preparation 1.4 as starting reagent.

A yield of 97% is obtained. TLC Rf=0.89 (CHCl$_3$/MeOH, 9:1), HPLC Rt=24.84 min.

PREPARATION 2.3: NHBocCys[S—S—(CH$_2$)$_{11}$CH$_3$]—NH(CH$_2$)$_{17}$CH$_3$

The synthesis is identical to preparation 2.1 but using the product of preparation 1.4 as starting reagent.

A yield of 86% is obtained. TLC Rf=0.90 (CHCl$_3$/MeOH, 9:1), HPLC Rt=22.22 min.

PREPARATION 2.4: NHBocCys[S—S—(CH$_2$)$_{11}$CH$_3$]—N[(CH$_2$)$_{17}$CH$_3$]$_2$

The synthesis is identical to preparation 2.1 but using dioctadecylamine and the product of preparation 1.4 as starting reagents.

A yield of 85% is obtained. TLC Rf=0.90 (CHCl$_3$/MeOH, 9:1).

PREPARATION 2.5: NHBocCys [S—S-Cholesterol]—NH(CH$_2$)$_{17}$CH$_3$

The synthesis is identical to preparation 2.1 but using octadecylamine and the product of preparation 1.3 as starting reagents.

A yield of 90% is obtained. TLC Rf=0.88 (CHCl$_3$/MeOH, 9:1) HPLC Rt=26.98 min.

STEP 3

PREPARATION 3.1 [compound (I)]: NH$_2$(CH$_2$)$_3$NH(CH$_2$)$_4$NH(CH$_2$)$_3$NHCH$_2$COCys-[S—S—(CH$_2$)$_4$CH$_3$]—N[(CH$_2$)$_{17}$CH$_3$]$_2$ Trifluoroacetic acid (10 cm$^3$) is added to the product of preparation 2.1. The medium is stirred for 1.5 hours and the cleavage of BOC is monitored by HPLC. The trifluoroacetic acid is evaporated off and to drive off the traces, 3 times 5 ml of diethyl ether are evaporated off.

The dry extract is dissolved in 10 cm$^3$ of dichloromethane and then N-ethyldiisopropylamine (3.34 mmol), BocNH(CH$_2$)$_3$ NBoc(CH$_2$)$_4$ NBoc(CH$_2$)$_3$ NBocCH$_2$CO$_2$H (0.644 mmol) and BOP (0.708 mmol) are added. The mixture is stirred for 2 hours and the reaction is monitored by TLC and HPLC.

The dichloromethane is evaporated off in a rotary evaporator. The crude product is taken up in chloroform (100 cm$^3$) and then washed successively with 3 times 50 cm$^3$ of 0.5 M KHSO$_4$, and then with 3 times 50 cm$^3$ of a saturated NaHCO$_3$ solution, and finally with twice 50 cm$^3$ of a saturated NaCl solution. The organic phase is dried over anhydrous magnesium sulphate and then the chloroform is evaporated off in a rotary evaporator.

Trifluoroacetic acid (10 cm$^3$) is added to the dry extract. The medium is stirred for 1.5 hours and the cleavage of the BOCs is monitored by HPLC. The trifluoroacetic acid is evaporated off and to drive off the traces, 3 times 5 cm$^3$ of diethyl ether are evaporated off.

The crude product obtained is purified by preparative HPLC. The fractions of interest are combined and freeze-dried. 0.081 mmol of salified product is obtained, that is a yield of 11%.

HPLC Rt=17.79 min. $^1$H NMR spectrum (400 MHz, (CD$_3$)$_2$SO-d$_6$, δ in ppm): 0.90 (mt, 9H: CH$_3$ of the two octadecylamino groups and CH$_3$ of the pentyldisulphanyl);

from 1.15 to 1.50 (mt, 64H: 15 $CH_2$ of one of the two octadecylamino groups—15 $CH_2$ of the other octadecylamino) and 2 $CH_2$ of the pentyldisulphanyl); 1.47 (mt, 2H: 1 $CH_2$ of one of the two octadecylamino groups); from 1.55 to 1.75 (mt, 4H: 1 $CH_2$ of one of the two octadecylamino groups and 1 $CH_2$ of the pentyldisulphanyl); 1.65 (mf, 4H: the 2 central $CH_2$ groups of the butyl); from 1.85 to 2.05 (mt, 4H: the central $CH_2$ of the two propyls); from 2.70 to 2.85 (mt, 1H: 1H of the $CH_2S$ of the cysteine); 2.78 (mt, 2H: $SCH_2$ of the pentyldisulphanyl); from 2.85 to 3.50 (mt: the 2 $NCH_2$ groups of the butyl—the 2 $NCH_2$ of the two propyls—the other H of the $CH_2S$ of the cysteine and the $NCH_2$ of the two octadecylamino groups); 3.80 (broad s, 2H: $NCH_2CON$ of the glycylamino); 5.07 (mt, 1H: CONCHCON of the cysteine); 9.05 (d, J=8 Hz, 1H: CONH of the cysteine); 7.95–8.85 and from 8.90 to 9.15 (respectively 2 unres. comp. and broad unres. comp.: the H atoms corresponding to the NH and $NH_2$ groups). $MH^+=969$ PREPARATION 3.2 [compound (II)]:

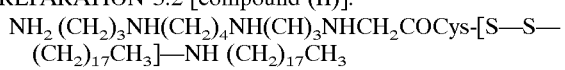

The procedure is identical to that described in preparation 3.1, but starting with the product obtained in preparation 2.2.

A yield of 31% of salified product is obtained. HPLC Rt=15.63 min. $^1H$ NMR spectrum (400 MHz, $(CD_3)_2SO$-$d_6$, δ in ppm): 0.89 (t, J=7.5 Hz, 6H: $CH_3$ of the octadecylamino and $CH_3$ of the octadecyldisulphanyl); from 1.15 to 1.45 (mt, 60H: 15 $CH_2$ of the octadecylamino) and 15 $CH_2$ of the octadecyldisulphanyl); 1.42 (mt: 1 of the $CH_2$ groups of the octadecylamino); from 1.55 to 1.70 (mt, 2H: 1 of the $CH_2$ groups of the octadecyldisulphanyl); 1.66 (unres. comp., 4H: the 2 central $CH_2$ groups of the butyl); from 1.85 to 2.05 (mt, 4H: the central $CH_2$ of the two propyls); 2.76 (t, J=7.5 Hz, 2H: $SCH_2$ of the octadecyldisulphanyl); from 2.85 to 3.10 (mt, 14H: the 2 $NCH_2$ of the butyl—the 2 $NCH_2$ of the two propyls—1H of the $NCH_2$ of the octadecylamino and 1H of the $CH_2S$ of the cysteine); 3.10 (dd, J=13.5 and 6 Hz, 1H: the other H of the $CH_2S$ of the cysteine); 3.18 (mt, 1H: the other H of the $NCH_2$ of the octadecylamino); 3.82 (very limiting AB; 2H: $NCH_2CON$ of the glycylamino); 4.60 (mt, 1H: CONCHCON of the cysteine); 8.27 (t, J=5.5 Hz, 1H: CONH of the octadecylamino); 8.90 (d, J=8.5 Hz, 1H: CONH of the cysteine); 7.95–8.82 and 9.07 (3 unres. comp.: the H atoms corresponding to the NH and $NH_2$ groups). $MH^+=899$.

PREPARATION 3.3 [compound (III)]: $NH_2(CH_2)_3NH(CH_2)_4NH(CH_2)_3NHCH_2COCys$-[S—S—$(CH_2)_{11}CH_3$]—$NH(CH_2)_{17}CH_3$ The procedure is identical to that described in preparation 3.1, but starting with the product obtained in preparation 2.3.

A yield of 26.5% of salified product is obtained. HPLC Rt=12.36 min. $^1H$ NMR spectrum (400 MHz, $(CD_3)_2SO$-$d_6$, δ in ppm): 0.90 (t, J=7.5 Hz, 6H: $CH_3$ of the octadecylamino and $CH_3$ of the dodecyldisulphanyl); from 1.15 to 1.50 (mt, 48H: 15 $CH_2$ of the octadecylamino and 9 $CH_2$ of the dodecyldisulphanyl); 1.43 (mt: 1 $CH_2$ of the octadecylamino); from 1.55 to 1.70 (mt, 2H: 1 $CH_2$ of the dodecyldisulphanyl); 1.65 (unres. comp., 4H: the 2 central $CH_2$ groups of the butyl); from 1.85 to 2.05 (mt, 4H: the central $CH_2$ of the two propyls); 2.76 (t, J=7.5 Hz, 2H: $SCH_2$ of the dodecyldisulphanyl); 2.80 to 3.05 (mt, 14H: the 2 $NCH_2$ of the butyl—the 2 $NCH_2$ of the two propyls—1H of the $NCH_2$ of the octadecylamino and 1H of the $CH_2S$ of the cysteine); 3.11 (dd, J=13.5 and 6 Hz, 1H: the other H of the $CH_2S$ of the cysteine); 3.17 (mt, 1H: the other H of the $NCH_2$ of the octadecylamino); 3.83 (limiting AB, 2H: $NCH_2CON$ of the glycylamino); 4.60 (mt, 1H: CONCHCON of the cysteine); 8.25 (t, J=5.5 Hz , 1H: CONH of the octadecylamino); 8.99 (d, J=8.5 Hz, 1H: CONH of the cysteine); 7.96–8.84 and 9.09 (3 unres. comp.: the H atoms corresponding to the NH and $NH_2$ groups). $MH^+=815$.

PREPARATION 3.4 [compound (IV)]: $NH_2(CH_2)_3NH(CH_2)_4NH(CH_2)_3NHCH_2COCys$-[S—S—$(CH_2)_{11}CH_3$]—$N[(CH_2)_{17}CH_3]_2$ The product obtained by preparation 2.4 is used in a synthesis identical to preparation 3.1.

A yield of 39% of salified product is obtained. HPLC Rt=19.75 min. $^1H$ NMR spectrum (400 MHz, $(CD_3)_2SO$-$d_6$, δ in ppm): 0.87 (t, J=7.5 Hz, 9H: $CH_3$ of the two octadecylamino groups and $CH_3$ of the dodecyldisulphanyl); from 1.15 to 1.50 (mt, 78H: 15 $CH_2$ of one of the two octadecylamino groups—15 $CH_2$ of the other octadecylamino) and 9 $CH_2$ of the dodecyldisulphanyl); 1.47 (mt, 2H: 1 $CH_2$ of one of the two octadecylamino groups) from 1.50 to 1.70 (mt, 4H: 1 $CH_2$ of one of the two octadecylamino groups and 1 $CH_2$ of the dodecyldisulphanyl); 1.68 (unres. comp., 4H: the 2 central $CH_2$ groups of the butyl); from 1.85 to 2.10 (mt, 4H: the central $CH_2$ of the two propyls); 2.77 (t, J=7.5 Hz, 2H: $SCH_2$ of the dodecyldisulphanyl); 2.80 (mt, 1H: 1H of the $CH_2S$ of the cysteine); from 2.70 to 3.50 (mt: the 2 $NCH_2$ of the butyl—the 2 $NCH_2$ of the two propyls—the other H of the $CH_2S$ of the cysteine and the $NCH_2$ of the two octadecylamino groups); 3.80 (broad s, 2H: $NCH_2CON$ of the glycylamino); 5.05 (mt, 1H: CONCHCON of the cysteine); 9.07 (d, J=8 Hz, 1H: CONH of the cysteine); from 7.75 to 8.20 and from 8.65 to 9.25 (2 broad unres. comp.: the H atoms corresponding to the NH and $NH_2$ groups). $MH^+=1067$.

PREPARATION 3.5 [compound (V)]: $NH_2(CH_2)_3NH(CH_2)_4NH(CH_2)_3NHCH_2COCyS$-[S—S-Cholesterol]—$NH(CH_2)_{17}CH_3$ The product obtained by preparation 2.5 is used in a synthesis identical to preparation 3.1 except for the final cleavage of the BOC groups for which the following mixture is used: 10 $cm^3$ of TFA, 0.5 ml of water, 0.5 ml of thioanisole and 0.75 g of phenol.

A yield of 5.6% of salified product is obtained. HPLC Rt=16.59 min. $^1H$ NMR spectrum (400 MHz, $(CD_3)_2SO$-$d_6$, at a temperature of 383 K, δ in ppm): 0.74 and 1.05 (2 s, 3H each: $CH_3$ in 18 and $CH_3$ in 19 of the cholesteryl); from 0.80 to 0.95 (mt: the H atoms corresponding to the $CH_3$ of the octadecylamino and to the $CH_3$ in 26—$CH_3$ in 27 and $CH_3$ in 21 of the cholesteryl); 1.77 (mt: the 4H atoms corresponding to the 2 central $CH_2$ groups of the butyl); from 1.85 to 2.10 (mt: the 4H atoms corresponding to the central $CH_2$ of the two propyls); from 2.90 to 3.25 (mt: the 16H atoms corresponding to the 2 $NCH_2$ of the butyl—to the 2 $NCH_2$ of the two propyls—to the $CH_2S$ of the cysteine and to the $NCH_2$ of the octadecylamino); 3.63 (limiting AB, 2H: $NCH_2CON$ of the glycylamino); 4.61 (mt, 1H: CONCHCON of the cysteine); 5.39 (mt, 1H: CH in 6 of the cholesteryl); 7.69 (mt, 1H: CONH of the octadecylamino); 8.25 (unres. comp., 1H: CONH of the cysteine). For all the other protons of the cholesteryl and of the octadecylamino, the corresponding signals come out between 0.60 and 3.00 ppm. $MH^+=1015$.

b) Symmetric Transfer Agents Which can be Separated by a Disulphide Bridge

These molecules of general structure:
Polyamine — Spacer — Lipid
          |
          S
          |
          S
          |
    aie — Spacer — Lipid
were constructed in the following manner:
Step 1)
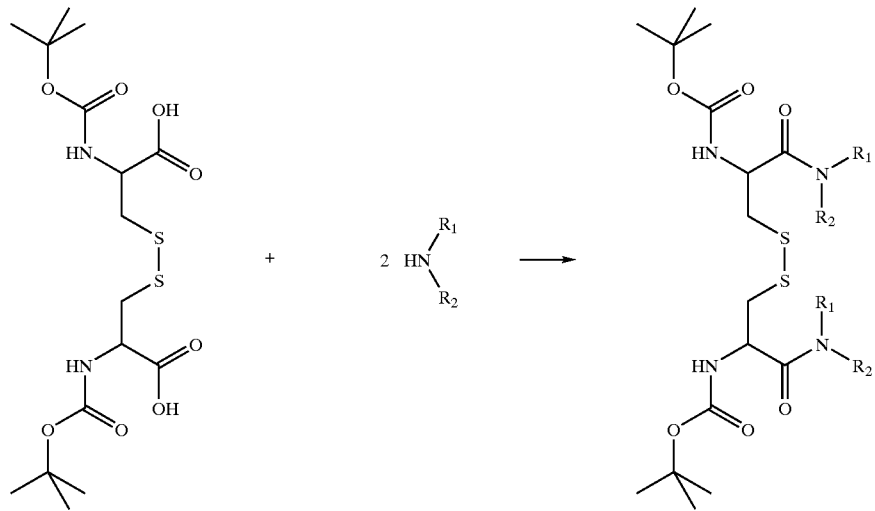
Step 2)
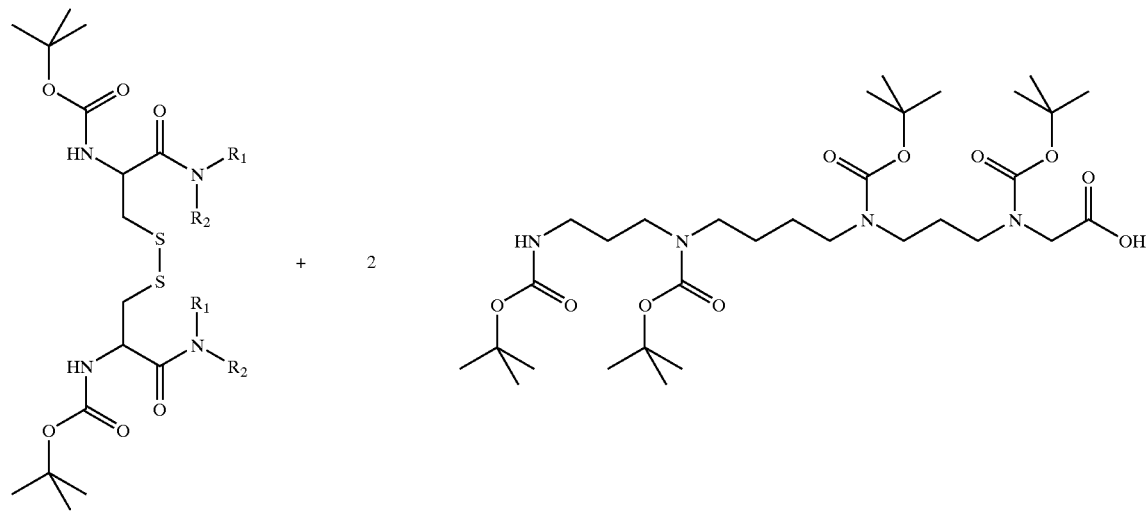

a) TFA
b) BOP, DIEA/CH2Cl2
c) TFA

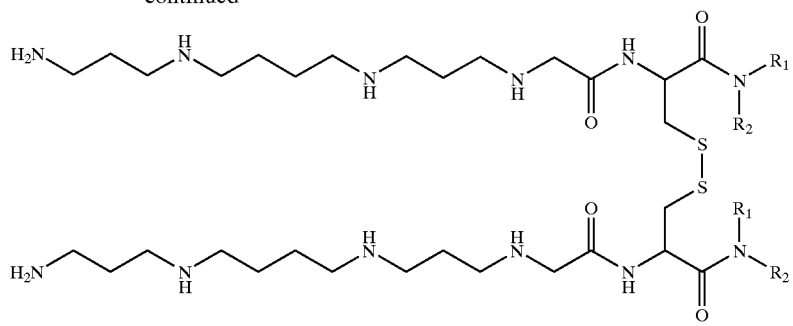

The following example, given with no limitation being implied, illustrates one of these transfer agents: compound (VI): $R_1=(CH_2)_{17}CH_3$; $R_2=H$

STEP 1

PREPARATION 1: [NHBoc-CH(CO—NH(CH$_2$)$_{17}$CH$_3$)CH$_2$—S—]$_2$ $N_\alpha,N_\alpha'$-diBoc-cystine (0.57 mmol) is dissolved in chloroform (15 cm$^3$) and N-ethyldiisopropylamine (5.67 mmol), octadecylamine (0.10 mmol) and BOP (1.24 mmol) are added.

The mixture is stirred for 2 hours and monitored by TLC and HPLC.

The chloroform is evaporated off in a rotary evaporator. The "crude product" is taken up in ethyl acetate (100 cm$^3$) and then washed successively with 3 times 50 cm$^3$ of 0.5 M KHSO$_4$ and then with 3 times 50 cm$^3$ of a saturated NaHCO$_3$ solution, and finally with twice 50 cm$^3$ of a saturated NaCl solution. The organic phase is dried over anhydrous magnesium sulphate and then the ethyl acetate is evaporated off in a rotary evaporator. 0.346 mmol of product is obtained, that is a yield of 69%. TLC Rf=0.94 (CHCl$_3$/MeOH, 9:1).

STEP 2

PREPARATION 2 [compound (VI)]: [NH$_2$(CH$_2$)$_3$NH (CH$_2$)$_4$NH (CH$_2$)$_3$NHCH$_2$CO—CyNH (CH$_2$)$_{17}$CH$_3$]$_2$ Trifluoroacetic acid (5 cm$^3$) is added to the product obtained by preparation 1. The mixture is stirred for 1.5 hours and the cleavage of the BOC is monitored by HPLC. The trifluoroacetic acid is evaporated off, and to drive off the traces, 3 times 5 cm$^3$ of diethyl ether are evaporated off.

The dry extract is dissolved in dichloromethane (25 cm$^3$), and then N-ethyl—diisopropylamine (3.44 mmol), BocNH(CH$_2$)$_3$ NBoc(CH$_2$)$_4$ NBoc(CH$_2$)$_3$ NBocCH$_2$CO$_2$H (0.697 mmol) and BOP (0.86 mmol) are added. The mixture is stirred for 2 hours and the reaction is monitored by TLC and HPLC.

The dichloromethane is evaporated off in a rotary evaporator. The "crude product" is taken up in ethyl acetate (100 cm$^3$) and is then washed successively with 3 times 50 cm$^3$ of 0.5 M KHSO$_4$ and then with 3 times 50 cm$^3$ of a saturated NaHCO$_3$ solution, and finally with twice 50 cm$^3$ of a saturated NaCl solution. The organic phase is dried over anhydrous magnesium sulphate and then the ethyl acetate is evaporated off in a rotary evaporator. TLC Rf=0.90 (CHCl$_3$/MeOH, 9:1), HPLC Rt=26.10 min.

Trifluoroacetic acid (5 cm$^3$) is added to the dry extract. The mixture is stirred for 1.5 hours and the cleavage of the BOC groups is monitored by HPLC. The trifluoroacetic acid is evaporated off, and to drive off the traces, 3 times 5 cm$^3$ of diethyl ether are evaporated off.

The crude product obtained is purified by preparative HPLC. The fractions of interest are combined and freeze-dried.

0.099 mmol of salified product is obtained, that is a yield of 28.5%, HPLC Rt=10.55 min. $^1$H NMR spectrum (400 MHz, (CD$_3$)$_2$SO-d$_6$, δ in ppm): 0.91 (t, J=7.5 Hz, 6H: CH$_3$ of the two octadecylamino groups); from 1.10 to 1.40 (mt, 60H: 15 CH$_2$ of one of the two octadecylamino groups and 15 CH$_2$ of the other octadecylamino); 1.43 (mt, 4H: 1 CH$_2$ of the two octadecylamino groups); 1.64 (unres. comp., 8H: the 2 central CH$_2$ groups of the two butyls); from 1.85 to 2.10 (mt, 8H: the central CH$_2$ of the four propyls); from 2.80 to 3.15 (mt, 32H: the 2 NCH$_2$ of the two butyls—the 2 NCH$_2$ of the four propyls—the NCH$_2$ of the two octadecylamino groups and the CH$_2$S of the two cysteines); 3.84 (unres. comp., 4H: the NCH$_2$CON of the two glycylamino groups); 4.60 (mt, 2H: the CONCHCON of the two cysteines); 8.27 (unres. comp., 2H: the CONH of the two octadecylamino groups); 8.95 (unres. comp., 2H: the CONH of the two cysteines); 7.97–8.87 and 9.15 (3 unres. comp.: the H atoms corresponding to the NH. and NH$_2$ groups). MH$^+$=1227.

Example 2

Evaluation of the Detergent Action of the Transfer Agents According to the Invention The objective of this example is to show that the transfer agents according to the invention possess detergent properties, that is to say that they are capable of dissolving the membranes.

For that, an in vitro model is used which represents the biological membranes, namely liposomes EPC/EPA (egg phosphatidylcholine/egg phosphatidic acid, 10:1). Just like biological membranes, the walls of these liposomes consist of phospholipid bilayers, and they therefore possess a comparable behaviour.

These liposomes are formed by dissolving the various constituents in chloroform, and then evaporating the said chloroform with the aid of a rotary evaporator. The lipid film obtained is redispersed in water, and then the liposomes are formed by sonication and heating.

The evaluation of the detergent action of the product added to the liposomes is made by measuring the turbidity with the aid of a spectrophotometer.

By way of reference, a first experiment was carried out with Triton X-100 which a well known commercially available detergent. Complete solubilization of the liposomes (100% solubilization) is then obtained as represented on the curve of FIG. 1.

The second product tested is an amphiphilic molecule comprising a polyamine connected through a spacer to a fatty chain containing 18 carbon atoms (compound (VII)). It therefore corresponds to the molecule obtained by reducing the disulphide bridge of the compound (II) of the present invention. The curve represented in FIG. 2 shows the results obtained when this amphiphilic molecule is added to the liposomes: a partial solubilization is observed which corresponds to a solubilization of about 30% compared with Triton X-100.

Finally, the same experiment was performed with the reference cationic lipid REF, namely the analogue of the compound (II) but containing no disulphide bridge. No solubilization of the liposomial membranes was observed.

In conclusion, this example shows that the transfer agents according to the invention are capable of generating, in reducing medium, amphiphilic molecules having a detergent action, that is to say capable of dissolving the membranes. This property is extremely advantageous because the transfer agents of the invention make it possible to vectorize nucleic acids in a larger quantity and more easily up to the cellular compartments, which allows improvement of the transfection efficiency (as is shown in the transfection examples which follow).

Example 3

Use of the Products According to the Invention for the In Vitro Transfection of Genetic Material These tests illustrate the capacity of the transfer agents according to the invention to efficiently transfect cells in vitro in spite of the insertion of disulphide bridge(s) into their structure.

A. GENETIC MATERIAL USED

The plasmid used is described in Patent WO 97/10343. This construct pCOR_pXL2774 comprises the gene encoding luciferase under the human cytomegalovirus very early gene promoter [hCMV-IE].

The nucleic acid solutions are diluted to 20 $\mu$g/ml in physiological saline (0.15 M NaCl).

B. CYTOFECTANT SOLUTIONS (prepared immediately before use)

The products described in the invention are dissolved in water at a concentration varying from 40 to 160 $\mu$mol and mixed volume for volume with the DNA solution. The final saline concentration is 75 mmol.

C. TRANSFECTION

The cells are cultured under appropriate conditions in 24-well microplates (2 cm$^2$/well) and are transfected while they are in the exponential growth phase and at 50–70% confluence.

The cells are washed with twice 0.5 cm$^3$ of medium free of serum proteins and grown again either in serum-free medium (transfection in the absence of serum), or in complete medium (transfection in the presence of serum) 0.05 cm$^3$ of cytofectant mixture (0.5 $\mu$g DNA/well) are added to the cells (3 wells/condition DNA vector). When the cells are transfected in the absence of serum, the growth medium is supplemented 2 hours after transfection with the appropriate quantity of serum.

The transfection efficiency is evaluated 48 hours post-transfection by measuring the expression of luciferase according to the recommendations given for the use of the Promega kit (Luciferase Assay System). The toxicity of the cytofectant mixtures is estimated by a measurement of the protein concentrations in the cell lysates.

D. RESULTS a) Symmetric Transfer Agents Which can be Separated by Reduction of a Disulphide Bridge: Compound (VI) (FIG. 3)

This product, described in the invention, was used in comparison with the reference cationic lipid REF (described as being compound (6) in Patent Application WO 97/18185) as DNA vector, to transfect the cell line HepG2.

For this cell type, the toxicity of the compound (VI) is of the same order of magnitude as that of the reference cationic liquid REF: when the transfection is carried out in the absence of serum proteins, the survival is 80% for the HepG2 cells, for cationic lipid doses of 160 $\mu$M.

The maximum transfection efficiency is obtained for a cationic lipid/$\mu$g of DNA ratio of 4 to 8 nanomoles. The transgene expression obtained with the use of compound (VI) in comparison with that obtained with the reference cationic lipid REF is higher (4 times) for transfections of HepG2 cells.

b) Transfer Agents Whose Lipid Part is Composed of Two $C_{18}$ Alkyl Chains and of a Third Alkyl Chain Linked by a Disulphide Bridge: Compounds (I) and (IV)

These two products, described in the present invention, exhibit no significant toxicity up to 160 $\mu$M of cationic lipid, both for HeLa cells and for HepG2 cells.

Compared with the expressions of the transgene obtained with the reference cationic lipid REF, the addition of a third $C_5$ lipid chain [compound (I)] makes it possible to obtain transfection results in the absence of serum proteins which are of the same order of magnitude. On the other hand, under the same transfection conditions, if the third lipid chain is a $C_{12}$ chain [compound (IV)], the expression of the transgene is increased by a factor of about 2-fold for the HeLa cells and of about 9-fold for the HepG2 cells (see FIG. 4).

Furthermore, one of the major advantages of increasing the lipophilicity of the cationic lipids by adding a third alkyl chain is demonstrated in transfection experiments in the presence of serum proteins. In this case, there is indeed no significant inhibition due to the presence of the serum proteins, which makes them preferred candidates for in vivo transfections.

FIGS. 5 and 6 represent, in the form of histograms, the transfection efficiency of compounds (I) and (IV).

c) Transfer Agents Whose Lipid Part is Composed of Two $C_{18}$ Alkyl Chains of Which One is Linked by a Disulphide Bridge: Compound (II)

This product, which is described in the invention, exhibits no significant toxicity at the doses used to the HepG2 cells (160 $\mu$M of cationic lipid).

For transfections in the absence of serum proteins, the level of the expression of the transgene is up to 3-fold higher compared with the reference cationic lipid REF (see FIG. 7). Furthermore, the transfection is clearly improved (up to 40-fold) in the presence of serum proteins. Therefore, quite unexpectedly, there is no inhibitory effect due to the presence of serum.

FIG. 8 represents, in the form of a histogram, the transfection efficiency of compounds (II).

d) Transfer Agents Whose Lipid Part Contains a Chain Derived From a Steroid Linked by a Disulphide Bridge: Compound (V) (FIG. 9)

This compound, which is described in the invention, exhibits no significant toxicity at the doses used to the HeLa or HepG2 cells (160 $\mu$M of cationic lipid).

The binding of a cholesterol instead of an alkyl chain provides a very significant gain as regards the expression of the transgene and furthermore, in this case, no inhibition could be observed in the presence of serum proteins, which makes this product very attractive for use in transfection in vivo.

In conclusion, the results presented in the tables and histograms of FIGS. 3 to 9 show that:

the introduction of disulphide bridge(s) into transfer agents of the cationic lipid type does not affect the capacity of these agents to transfect DNA in vitro, but leads, quite on the contrary, to an improvement in the transfection efficiency.

the transfer agents according to the invention are not toxic at the doses used, and finally, the increase in the lipophilicity of the transfer agents according to the invention makes it possible to remove, at least partially, the inhibition of the transfection due to serum.

What is claimed is:

1. A nucleic acid transfer agent comprising at least one cationic hydrophilic region capable of noncovalently combining with nucleic acids and at least one lipophilic region, these regions being connected to each other through a spacer arm, said transfer agent further comprising at least one disulphide bridge positioned either (A) in said lipophilic region, whereby reduction thereof generates a detergent amphiphilic molecule or (B) in the spacer arm between two symmetrical parts of said transfer agent, whereby reduction thereof causes separation of the two symmetrical parts of said transfer agent theretofore separated by said spacer arm.

2. A transfer agent according to claim 1, wherein the cationic hydrophilic region is a polyamine or a polyaminoguanidine.

3. A transfer agent according to claim 1, wherein the lipophilic region comprises at least one aliphatic fatty chain and at least one other chain selected from the group consisting of other aliphatic chains, steroid derivatives, natural and synthetic lipids, or a combination of such other chains.

4. A transfer agent according to claim 3, wherein the lipophilic region comprises at least two aliphatic fatty chains.

5. A transfer agent according to claim 3, wherein the lipophilic region comprises an aliphatic fatty chain and a steroid derivative.

6. A transfer agent according to claim 3, wherein said aliphatic fatty chain is an optionally fluorinated linear or branched alkyl chain comprising 10 to 22 carbon atoms.

7. A transfer agent according to claim 3, wherein the steroid derivative is selected from the group consisting of cholesterol, cholic acid and cholesterylamine.

8. A transfer agent according to claim 1, wherein the spacer arm is selected from the group consisting of amides, carbamates, esters, ethers and aromatic rings.

9. A transfer agent according to claim 1, which comprises one or two disulphide bridges.

10. A transfer agent according to claim 1, which comprises a disulphide bridge positioned such that its reduction causes the loss of an aliphatic fatty chain.

11. A transfer agent according to claim 3, which comprises a disulphide bridge positioned such that its reduction causes the loss of a chain derived from a steroid present in the lipophilic region.

12. A transfer agent selected from the group consisting of:
$NH_2(CH_2)_3NH(CH_2)_4NH(CH_2)_3NHCH_2COCys[S—S—(CH_2)_4CH_3]—N[CH_2)_{17}CH_3]_2$ (I);
$NH_2(CH_2)_3NH(CH_2)_4NH(CH_2)_3NHCH_2COCys[S—S—(CH_2)_{17}CH_3]—NH(CH_2)_{17}CH_3$ (II);
$NH_2(CH_2)_3NH(CH_2)_4NH(CH_2)_3NHCH_2COCys[S—S—(CH_2)_{11}CH_3]—NH(CH_2)_{17}CH_3$ (III);
$NH_2(CH_2)_3NH(CH_2)_4NH(CH_2)_3NHCH_2COCys[S—S—(CH_2)_{11}CH_3]—N[(CH_2)_{17}CH_3]_2$ (IV);
$NH_2(CH_2)_3NH(CH_2)_4NH(CH_2)_3NHCH_2COCys[S—S-Cholesterol]—NH(CH_2)_{17}CH_3$ (V); and
$[NH_2(CH_2)_3NH(CH_2)_4NH(CH_2)_3NHCH_2COCysNH(CH_2)_{17}CH_3]_2$ (VI).

13. A composition comprising a transfer agent as defined in claim 1 and at least one nucleic acid.

14. A composition according to claim 13, wherein the nucleic acid is a deoxyribonucleic acid or a ribonucleic acid.

15. A composition according to claim 13, wherein the nucleic acid is chemically modified.

16. A composition according to claim 13, wherein the nucleic acid comprises an anti-sense sequence.

17. A composition according to claim 13, wherein the nucleic acid comprises a therapeutic gene.

18. A composition according to claims 13 which further comprises an adjuvant consisting of at least one neutral lipid selected from the group consisting of synthetic and natural lipids which are zwitterionic or lack an ionic charge under physiological conditions.

19. A composition according to claim 18, wherein said neutral lipid is selected from the group consisting of cholesterol and lipids containing two fatty chains selected from the group consisting of dioleoylphosphatidylethanolamine (DOPE), oleoylpalmitoylphosphatidylethanolamine (POPE), di-stearoyl, -palmitoyl, -cholesteryl, -myristoylphosphatidylethanolamines as well as their derivatives which are N-methylated 1 to 3 times, phosphatidylglycerols, glycosyldiacylglycerols, cerebrosides, sphingolipids and asialogangliosides.

20. A composition which comprises (1) a nucleic acid transfer agent comprising at least one cationic hydrophilic region capable of noncovalently combining with nucleic acids and at least one lipophilic region, these regions being connected to each other through a spacer arm, said transfer agent further comprising at least one disulphide bridge positioned either (A) in said lipophilic region, whereby reduction thereof generates a detergent amphiphilic molecule or (B) in the spacer arm between two symmetrical parts of said transfer agent, whereby reduction thereof causes separation of the two symmetrical parts of said transfer agent theretofore separated by said spacer arm (2) at least one nucleic acid, and (3) an adjuvant which comprises a compound derived in whole or in part from at least one of a histone, a nucleolin and a protamine, or 2 to 10 peptide units selected from (KTPKKAKKP) and/or (ATPAKKAA) repeated in a continuous manner or otherwise.

21. A composition according to claim 13, which further comprises a targeting component.

22. A composition according to claim 21, wherein said targeting component is selected from the group consisting of antibodies directed against cell surface molecules, membrane receptor ligands, cytokines, vitamins, optionally modified lectins, proteins with an RGD unit, peptides containing a tandem of RGD units, cyclic or otherwise, polylysine peptides, and natural and synthetic ligand peptides.

23. A composition which comprises (1) a nucleic acid transfer agent comprising at least one cationic hydrophilic region capable of noncovalently combining with nucleic acids and at least one lipophilic region, these regions being connected to each other through a spacer arm, said transfer agent further comprising at least one disulphide bridge positioned either (A) in said lipophilic region, whereby reduction thereof generates a detergent amphiphilic molecule or (B) in the spacer arm between two symmetrical parts of said transfer agent, whereby reduction thereof causes separation of the two symmetrical parts of said transfer agent theretofore separated by said spacer arm (2) at least one nucleic acid and (3) at least one nonionic surfactant selected from the group consisting of poloxamers, polyoxyethylene alcohols, polyoxyethylene nonyl phenyl ether, and polyethylene glycols with a dendritic benzyl polyether head.

24. In a method of transferring nucleic acids into cells, the improvement which comprises use of a transfer agent as defined in claim 1.

25. A method of transferring nucleic acids into cells which comprises the following steps:
    (1) bringing the nucleic acid into contact with a transfer agent as defined in claim 1 to form a nucleic acid/transfer agent complex, and
    (2) bringing the cells into contact with the complex formed in (1).

26. A method of preparing a composition as defined in claim 13, wherein a nucleic acid is brought into contact with a transfer agent as defined in claim 1 to form a nucleic acid/transfer agent complex.

27. A composition according to claim 22 wherein said membrane receptor ligands are selected from the group consisting of insulin, transferrin, folic acid and any other growth factors.

28. A composition which comprises (1) a nucleic acid transfer agent comprising at least one cationic hydrophilic region capable of noncovalently combining with nucleic acids and at least one lipophilic region, these regions being connected to each other through a spacer arm said transfer agent further comprising at least one disulphide bridge positioned either (A) in said lipophilic region, whereby reduction thereof generates a detergent amphiphilic molecule or (B) in the spacer arm between two symmetrical parts of said transfer agent, whereby reduction thereof causes separation of the two symmetrical parts of said transfer agent theretofore separated by said spacer arm, (2) at least one nucleic acid and (3) a galactocerebroside.

29. A composition which comprises (1) a nucleic acid transfer agent comprising at least one cationic hydrophilic region capable of noncovalently combining with nucleic acids and at least one lipophilic region, these regions being connected to each other through a spacer arm, said transfer agent further comprising at least one disulphide bridge positioned either (A) in said lipophilic region, whereby reduction thereof generates a detergent amphiphilic molecule or (B) in the spacer arm between two symmetrical parts of said transfer agent, whereby reduction thereof causes separation of the two symmetrical parts of said transfer agent theretofore separated by said spacer arm, (2) at least one nucleic acid and (3) a sphingomyelin.

30. A composition which comprises (1) a nucleic acid transfer agent comprising at least one cationic hydrophilic region capable of noncovalently combining with nucleic acids and at least one lipophilic region, these regions being connected to each other through a spacer arm, said transfer agent further comprising at least one disulphide bridge positioned either (A) in said lipophilic region, whereby reduction thereof generates a detergent amphiphilic molecule or (B) in the spacer arm between two symmetrical parts of said transfer agent, whereby reduction thereof causes separation of the two symmetrical parts of said transfer agent theretofore separated by said spacer arm, (2) at least one nucleic acid and (3) an asiaganglioside selected from the group consisting of asioloGMI and asioloGM2.

* * * * *